US008606360B2

(12) United States Patent
Butson et al.

(10) Patent No.: US 8,606,360 B2
(45) Date of Patent: Dec. 10, 2013

(54) SYSTEMS AND METHODS FOR DETERMINING VOLUME OF ACTIVATION FOR SPINAL CORD AND PERIPHERAL NERVE STIMULATION

(75) Inventors: Christopher R. Butson, Wauwatosa, WI (US); Christopher B. Maks, Yardley, PA (US); Cameron C. McIntyre, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 543 days.

(21) Appl. No.: 12/662,722

(22) Filed: Apr. 30, 2010

(65) Prior Publication Data
US 2011/0066407 A1    Mar. 17, 2011

Related U.S. Application Data

(63) Continuation-in-part of application No. 11/715,829, filed on Mar. 8, 2007, now Pat. No. 8,180,601.

(60) Provisional application No. 60/743,445, filed on Mar. 9, 2006.

(51) Int. Cl.
*A61N 1/00* (2006.01)
(52) U.S. Cl.
USPC .......................................................... 607/45
(58) Field of Classification Search
USPC ............................................. 607/45–46, 117
See application file for complete search history.

(56) References Cited

U.S. PATENT DOCUMENTS

| | | | |
|---|---|---|---|
| 4,341,221 | A | 7/1982 | Testerman |
| 5,099,846 | A | 3/1992 | Hardy |
| 5,344,438 | A | 9/1994 | Testerman et al. |
| 5,361,763 | A | 11/1994 | Kao et al. |
| 5,452,407 | A | 9/1995 | Crook |
| 5,560,360 | A | 10/1996 | Filler et al. |
| 5,782,762 | A | 7/1998 | Vining |

(Continued)

FOREIGN PATENT DOCUMENTS

| | | |
|---|---|---|
| EP | 1372780 A2 | 10/2002 |
| WO | WO-02065896 A2 | 8/2002 |
| WO | WO-03086185 A1 | 10/2003 |
| WO | WO-2006017053 A1 | 2/2006 |

OTHER PUBLICATIONS

""BioPSE" The Biomedical Problem Solving Environment", http://www.sci.utah.edu/cibc/software/index.html, NCRR Center for Integrative Biomedical Computing,(2004).

(Continued)

*Primary Examiner* — Eric D. Bertram
*Assistant Examiner* — Roland Dinga
(74) *Attorney, Agent, or Firm* — Kenyon & Kenyon LLP

(57) ABSTRACT

This document discloses, among other things, systems and methods for determining volume of activation for spinal cord stimulation ("SCS") using a finite element model (FEM) circuit to determine a FEM of an implanted electrode and a spinal cord in which the electrode is implanted, a Fourier FEM solver circuit to calculate a potential distribution in the spinal cord using information from the FEM circuit and a capacitive component of at least one of the implanted electrode and the spinal cord, and a volume of activation (VOA) circuit to predict a VOA using the potential distribution and a neuron model.

22 Claims, 19 Drawing Sheets
(8 of 19 Drawing Sheet(s) Filed in Color)

(56) References Cited

U.S. PATENT DOCUMENTS

| | | | |
|---|---|---|---|
| 5,938,688 A | 8/1999 | Schiff | |
| 6,066,163 A | 5/2000 | John | |
| 6,083,162 A | 7/2000 | Vining | |
| 6,106,460 A | 8/2000 | Panescu et al. | |
| 6,146,390 A | 11/2000 | Heilbrun et al. | |
| 6,240,308 B1 | 5/2001 | Hardy et al. | |
| 6,289,239 B1 | 9/2001 | Panescu et al. | |
| 6,301,492 B1 | 10/2001 | Zonenshayn | |
| 6,310,619 B1 | 10/2001 | Rice | |
| 6,343,226 B1 | 1/2002 | Sunde et al. | |
| 6,351,675 B1 | 2/2002 | Tholen et al. | |
| 6,353,762 B1* | 3/2002 | Baudino et al. | 607/45 |
| 6,389,311 B1 | 5/2002 | Whayne et al. | |
| 6,421,566 B1 | 7/2002 | Holsheimer | |
| 6,463,328 B1 | 10/2002 | John | |
| 6,491,699 B1 | 12/2002 | Henderson et al. | |
| 6,539,263 B1 | 3/2003 | Schiff et al. | |
| 6,560,490 B2 | 5/2003 | Grill et al. | |
| 6,622,048 B1 | 9/2003 | Mann et al. | |
| 6,675,046 B2 | 1/2004 | Holsheimer | |
| 6,690,972 B2 | 2/2004 | Conley et al. | |
| 6,694,162 B2 | 2/2004 | Hartlep | |
| 6,694,163 B1 | 2/2004 | Vining | |
| 6,748,098 B1 | 6/2004 | Rosenfeld | |
| 6,788,969 B2 | 9/2004 | Dupree et al. | |
| 6,827,681 B2 | 12/2004 | Tanner et al. | |
| 6,830,544 B2 | 12/2004 | Tanner | |
| 6,909,913 B2 | 6/2005 | Vining | |
| 7,003,349 B1 | 2/2006 | Andersson et al. | |
| 7,008,370 B2 | 3/2006 | Tanner et al. | |
| 7,035,690 B2* | 4/2006 | Goetz | 607/46 |
| 7,043,293 B1 | 5/2006 | Baura | |
| 7,050,857 B2 | 5/2006 | Samuelsson et al. | |
| 7,107,102 B2 | 9/2006 | Daignault, Jr. et al. | |
| 7,136,518 B2 | 11/2006 | Griffin et al. | |
| 7,136,695 B2 | 11/2006 | Pless et al. | |
| 7,146,219 B2 | 12/2006 | Sieracki et al. | |
| 7,146,223 B1 | 12/2006 | King | |
| 7,167,760 B2 | 1/2007 | Dawant et al. | |
| 7,177,674 B2 | 2/2007 | Echauz et al. | |
| 7,181,286 B2 | 2/2007 | Sieracki et al. | |
| 7,184,837 B2 | 2/2007 | Goetz | |
| 7,216,000 B2 | 5/2007 | Sieracki et al. | |
| 7,218,968 B2 | 5/2007 | Condie et al. | |
| 7,231,254 B2 | 6/2007 | DiLorenzo | |
| 7,239,910 B2 | 7/2007 | Tanner | |
| 7,239,926 B2 | 7/2007 | Goetz | |
| 7,252,090 B2 | 8/2007 | Goetz | |
| 7,257,447 B2 | 8/2007 | Cates et al. | |
| 7,266,412 B2 | 9/2007 | Stypulkowski | |
| 7,324,851 B1 | 1/2008 | DiLorenzo | |
| 7,388,974 B2 | 6/2008 | Yanagita | |
| 7,463,928 B2 | 12/2008 | Lee et al. | |
| 7,499,048 B2 | 3/2009 | Sieracki et al. | |
| 7,505,815 B2 | 3/2009 | Lee et al. | |
| 7,548,786 B2 | 6/2009 | Lee et al. | |
| 7,603,177 B2 | 10/2009 | Sieracki et al. | |
| 7,617,002 B2 | 11/2009 | Goetz | |
| 7,623,918 B2 | 11/2009 | Goetz | |
| 7,657,319 B2 | 2/2010 | Goetz et al. | |
| 7,676,273 B2 | 3/2010 | Goetz et al. | |
| 2002/0062143 A1 | 5/2002 | Baudino et al. | |
| 2002/0123780 A1 | 9/2002 | Grill et al. | |
| 2002/0128694 A1 | 9/2002 | Holsheimer | |
| 2004/0044279 A1 | 3/2004 | Lewin et al. | |
| 2004/0044378 A1 | 3/2004 | Holsheimer | |
| 2004/0044379 A1 | 3/2004 | Holsheimer | |
| 2004/0106916 A1 | 6/2004 | Quaid et al. | |
| 2004/0199216 A1 | 10/2004 | Lee et al. | |
| 2004/0267330 A1 | 12/2004 | Lee et al. | |
| 2005/0033380 A1 | 2/2005 | Tanner et al. | |
| 2005/0070781 A1 | 3/2005 | Dawant et al. | |
| 2005/0085714 A1 | 4/2005 | Foley et al. | |
| 2005/0267347 A1 | 12/2005 | Oster | |
| 2006/0017749 A1* | 1/2006 | McIntyre et al. | 345/664 |
| 2006/0020292 A1 | 1/2006 | Goetz et al. | |
| 2006/0235472 A1 | 10/2006 | Goetz et al. | |
| 2006/0259079 A1 | 11/2006 | King | |
| 2007/0049817 A1 | 3/2007 | Preiss et al. | |
| 2007/0112402 A1* | 5/2007 | Grill et al. | 607/115 |
| 2007/0123953 A1 | 5/2007 | Lee et al. | |
| 2007/0156186 A1 | 7/2007 | Lee et al. | |
| 2007/0162086 A1 | 7/2007 | DiLorenzo | |
| 2007/0185544 A1 | 8/2007 | Dawant et al. | |
| 2007/0203538 A1 | 8/2007 | Stone et al. | |
| 2007/0203539 A1 | 8/2007 | Stone et al. | |
| 2007/0203540 A1 | 8/2007 | Goetz et al. | |
| 2007/0203541 A1 | 8/2007 | Goetz et al. | |
| 2007/0203543 A1 | 8/2007 | Stone et al. | |
| 2007/0203544 A1 | 8/2007 | Goetz et al. | |
| 2007/0203545 A1 | 8/2007 | Stone et al. | |
| 2007/0203546 A1 | 8/2007 | Stone et al. | |
| 2007/0213789 A1 | 9/2007 | Nolan et al. | |
| 2007/0213790 A1 | 9/2007 | Nolan et al. | |
| 2007/0244519 A1 | 10/2007 | Keacher et al. | |
| 2007/0245318 A1 | 10/2007 | Goetz et al. | |
| 2007/0255321 A1 | 11/2007 | Gerber et al. | |
| 2007/0255322 A1 | 11/2007 | Gerber et al. | |
| 2007/0276441 A1 | 11/2007 | Goetz | |
| 2007/0282189 A1 | 12/2007 | Dan et al. | |
| 2008/0027514 A1 | 1/2008 | DeMulling et al. | |
| 2008/0081982 A1 | 4/2008 | Simon et al. | |
| 2008/0103533 A1 | 5/2008 | Patel et al. | |
| 2008/0123922 A1 | 5/2008 | Gielen et al. | |
| 2008/0141217 A1 | 6/2008 | Goetz et al. | |
| 2008/0154340 A1 | 6/2008 | Goetz et al. | |
| 2008/0163097 A1 | 7/2008 | Goetz et al. | |
| 2008/0183256 A1 | 7/2008 | Keacher | |
| 2008/0215118 A1 | 9/2008 | Goetz et al. | |
| 2008/0269588 A1 | 10/2008 | Csavoy et al. | |
| 2009/0112289 A1 | 4/2009 | Lee et al. | |
| 2009/0149917 A1 | 6/2009 | Whitehurst et al. | |
| 2009/0196471 A1 | 8/2009 | Goetz et al. | |
| 2009/0196472 A1 | 8/2009 | Goetz et al. | |
| 2009/0198306 A1 | 8/2009 | Goetz et al. | |
| 2009/0276008 A1 | 11/2009 | Lee et al. | |
| 2009/0281595 A1 | 11/2009 | King et al. | |
| 2009/0281596 A1 | 11/2009 | King et al. | |
| 2009/0299164 A1 | 12/2009 | Singhal et al. | |
| 2009/0299165 A1 | 12/2009 | Singhal et al. | |
| 2009/0299380 A1 | 12/2009 | Singhal et al. | |
| 2010/0010646 A1 | 1/2010 | Drew et al. | |
| 2010/0049280 A1 | 2/2010 | Goetz | |
| 2011/0066407 A1 | 3/2011 | Butson et al. | |

OTHER PUBLICATIONS

"U.S. Appl. No. 10/885,982, Final Office Action mailed Aug. 9, 2007", 8 pgs.

"U.S. Appl. No. 10/885,982, Final Office Action mailed Dec. 12, 2006", 10 pgs.

"U.S. Appl. No. 10/885,982, Non-Final Office Action mailed Apr. 19, 2007", 17 pgs.

"U.S. Appl. No. 10/885,982, Non-Final Office Action mailed Apr. 21, 2006", 20 pgs.

"U.S. Appl. No. 10/885,982, Response filed Mar. 12, 2007 to Final Office Action mailed Dec. 12, 2006", 26 pgs.

"U.S. Appl. No. 10/885,982, Response filed Jul. 19, 2007 to Non-Final Office Action mailed Apr. 19, 2007", 19 pgs.

"U.S. Appl. No. 10/885,982, Response filed Jul. 21, 2006 to Non-Final Office Action mailed Apr. 21, 2006", 24 pgs.

et al., "Deep-brain stimulation of the subthalamic nucleus or the pars interna of the globus pallidus in Parkinson's disease", *N. Engl J Med.*, 345(13), Author: Deep-Brain Stimulation for Parkinson's Disease Study Group,(Sep. 27, 2001),956-963.

"International Search Report and Written Opinion for for Application No. PCT/US2005/023672, date mailed Jan. 20, 2006", 19 Pages.

Adler, D E., et al., "The tentorial notch: anatomical variation, morphometric analysis, and classification in 100 human autopsy cases", *J. Neurosurg.*, 96(6), (Jun. 2002),1103-1112.

Alexander, D C., et al., "Spatial transformations of diffusion tensor magnetic resonance images", *IEEE Transactions on Medical Imaging*, 20(11), (2001),1131-1139.

(56) References Cited

OTHER PUBLICATIONS

Alo, K. M., et al., "New trends in neuromodulation for the management of neuropathic pain", *Neurosurgery*, 50(4), (Apr. 2002),690-703; discussion 703-4.

Andrews, R. J., "Neuroprotection trek—the next generation: neuromodulation I. Techniques—deep brain stimulation, vagus nerve stimulation, and transcranial magnetic stimulation.", *Ann N Y Acad Sci.*, 993, (May 2003),1-13.

Andrews, R. J., "Neuroprotection trek—the next generation: neuromodulation II. Applications—epilepsy, nerve regeneration, neurotrophins.", *Ann N Y Acad Sci.*, 993, (May 2003),14-24.

Ashby, P , et al., "Neurophysiological effects of stimulation through electrodes in the human subthalamic nucleus", *Brain*, 122 ( Pt 10), (Oct. 1999),1919-1931.

Astrom, M. , et al., "The effect of cystic cavities on deep brain stimulation in the basal ganglia: a simulation-based study", *J Neural Eng.*, 3(2), (Jun. 2006),132-8.

Back, C. , et al., "Postoperative Monitoring of the Electrical Properties of Tissue and Electrodes in Deep Brain Stimulation", *Neuromodulation*, 6(4), (Oct. 2003),248-253.

Baker, K. B., et al., "Evaluation of specific absorption rate as a dosimeter of MRI-related implant heating", *J Magn Reson Imaging.*, 20(2), (Aug. 2004),315-20.

Baker, K. B., et al., "Subthalamic nucleus deep brain stimulus evoked potentials: Physiological and therapeutic implications", *Movement Disorders*, 17(5), (Sep./Oct. 2002),969-983.

Bammer, R , et al., "Diffusion tensor imaging using single-shot SENSE-EPI", *Magn Reson Med.*, 48(1), (Jul. 2002),128-136.

Basser, P J., et al., "MR diffusion tensor spectroscopy and imaging", *Biophys J.*, 66(1), (Jan. 1994),259-267.

Basser, P J., et al., "New currents in electrical stimulation of excitable tissues", *Annu Rev Biomed Eng.*, 2, (2000),377-397.

Bedard, C. , et al., "Modeling extracellular field potentials and the frequency-filtering properties of extracellular space", *Biophys J.*, 86(3), (Mar. 2004),1829-42.

Benabid, A L., et al., "Chronic electrical stimulation of the ventralis intermedius nucleus of the thalamus as a treatment of movement disorders", *J. Neurosurg.*, 84(2), (Feb. 1996),203-214.

Benabid, A L., et al., "Combined (thalamotoy and stimulation) stereotactic surgery of the VIM thalamic nucleus for bilateral Parkinson disease", *Appl. Neurophysiol*, vol. 50, (1987),344-346.

Benabid, A. L., et al., "Future prospects of brain stimulation", *Neurol Res.*, 22(3), (Apr. 2000),237-46.

Benabid, A L., et al., "Long-term suppression of tremor by chronic stimulation of the ventral intermediate thalamic nucleus", *Lancet*, 337(8738), (Feb. 16, 1991),403-406.

Brummer, S. B., et al., "Electrical Stimulation with Pt Electrodes: II—Estimation of Maximum Surface Redox (Theoretical Non-Gassing) Limits", *IEEE Transactions on Biomedical Engineering*, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the Volume of Activation", *Proceedings of the 2nd International IEEE EMBS*, (Mar. 16-19, 2005),196-197.

Butson, C. R., et al., "Deep brainstimulation interactive visualization system", *Society for Neuroscience*, vol. 898.7, (2005).

Butson, Christopher R., et al., "Patient-specific analysis of the volume of tissue activated during deep brain stimulation", *NeuroImage*, vol. 34, (2007),661-670.

Butson, C. R., et al., "Patient-specific models of deep brain stimulation: 3D visualization of anatomy, electrode and volume of activation as a function of the stimulation parameters.", *Soc Neurosci Abstr. 30*, (2004),1011.11.

Butson, C. R., et al., "Role of electrode design on the volume of tissue activated during deep brain stimulation", *J Neural Eng.*, 3(1), (Mar. 2006),1-8.

Butson, Christopher R., et al., "Sources and effects of electrode impedance during deep brain stimulation", *Clinical Neurophysiology*, vol. 117, (2006),447-454.

Butson, C. R., et al., "StimExplorer: Deep brain stimulation parameter selection software system", In: *Neuromodulation.*, DE Sakas, B Simpson and E Krames (eds), Springer-Verlag.,(2006),569-574.

Butson, Christopher R., et al., "Tissue and electrode capacitance reduce neural activaton volumes during deep brain stimulation", *Clinical Neurophysiology*, vol. 116, (2005),2490-2500.

Christensen, Gary E., et al., "Volumetric transformation of brain anatomy", *IEEE Transactions on Medical Imaging*, 16(6), (Dec. 1997),864-877.

Cooper, S , et al., "Differential effects of thalamic stimulation parameters on tremor and paresthesias in essential tremor", *Movement Disorders*, 17(Supp. 5), (2002),S193.

Coubes, P , et al., "Treatment of DYT1-generalised dystonia by stimulation of the internal globus pallidus", *Lancet*, 355(9222), (Jun. 24, 2000),2220-2221.

Dasilva, A.F. M., et al., "A Primer Diffusion Tensor Imaging of Anatomical Substructures", *Neurosurg. Focus*; 15(1), (Jul. 2003),1-4.

Dawant, B. M., et al., "Compuerized atlas-guided positioning of deep brain stimulators: a feasibility study", *Biomedical Image registration, Second International Workshop, WBIR 2003,*, Revised Papers (Lecture notes in Comput. Sci. vol. (2717), Springer-Verlag Berlin, Germany,(2003),142-150.

Finnis, K. W., et al., "3-D functional atalas of subcortical structures for image guided stereotactic neurosurgery", *Neuroimage*, vol. 9, Num. 6, Iss. 2, (1999),S206.

Finnis, K. W., et al., "3D Functional Database of Subcortical Structures for Surgical Guidance in Image Guided Stereotactic Neurosurgery", *Medical Image Computing and Computer-Assisted Intervention—MICCAI'99, Second International Conference*, Cambridge, UK, Sep. 19-22, 1999, *Proceedings*, (1999),758-767.

Finnis, K. W., et al., "A 3-Dimensional Database of Deep Brain Functional Anatomy, and Its Application to Image-Guided Neurosurgery", *Proceedings of the Third International Confernece on Medical Image Computing and Computer-Assisted Intervention, Lecture Notes in Computer Science*; vol. 1935, (2000),1-8.

Finnis, K. W., et al., "A functional database for guidance of surgical and therapeutic procedures in the deep brain", *Proceedings of the 22nd Annual International Conference of the IEEE Engineering in Medicine and Biology Society*, vol. 3, (2000),1787-1789.

Finnis, K. W., et al., "Application of a Population Based Electrophysiological Database to the Planning and Guidance of Deep Brain Stereotactic Neurosurgery", *Proceedings of the 5th International Conference on Medical Image Computing and Computer-Assisted Intervention—Part II, Lecture Notes in Computer Science*; vol. 2489, (2002),69-76.

Finnis, K. W., et al., "Subcortical physiology deformed into a patient-specific brain atlas for image-guided stereotaxy", *Proceedings of SPIE—vol. 4681 Medical Imaging 2002: Visualization, Image-Guided Procedures, and Display*, (May 2002),184-195.

Finnis, Krik W., et al., "Three-Dimensional Database of Subcortical Electrophysiology for Image-Guided Stereotatic Functional Neurosurgery", *IEEE Transactons on Medical Imaging*, 22(1), (Jan. 2003),93-104.

Foster, K. R., et al., "Dielectric properties of tissues and biological materials: a critical review.", *Crit. Rev Biomed Eng.*, 17(1), (1989),25-104.

Gabriels, L , et al., "Deep brain stimulation for treatment-refractory obsessive-compulsive disorder: psychopathological and neuropsychological outcome in three cases", *Acta Psychiatr Scand.*, 107(4), (2003),275-282.

Gabriels, L A., et al., "Long-term electrical capsular stimulation in patients with obsessive-compulsive disorder", *Neurosurgery*, 52(6), (Jun. 2003),1263-1276.

Geddes, L. A., et al., "The specific resistance of biological material—a compendium of data for the biomedical engineer and physiologist.", *Med Biol Eng.*, 5(3), (May 1967),271-93.

Gimsa, J. , et al., "Choosing electrodes for deep brain stimulation experiments—electrochemical considerations.", *J Neurosci Methods*, 142(2), (Mar. 30, 2005),251-65.

Goodall, E. V., et al., "Modeling study of activation and propagation delays during stimulation of peripheral nerve fibers with a tripolar

(56) References Cited

OTHER PUBLICATIONS cuff electrode", *IEEE Transactions on Rehabilitation Engineering*, [see also *IEEE Trans. on Neural Systems and Rehabilitation*], 3(3), (Sep. 1995),272-282.

Goodall, E. V., et al., "Position-selective activation of peripheral nerve fibers with a cuff electrode", *IEEE Transactions on Biomedical Engineering*, 43(8), (Aug. 1996),851-856.

Goodall, E. V., "Simulation of activation and propagation delay during tripolar neural stimulation", *Proceedings of the 15th Annual International Conference of the IEEE Engineering in Medicine and Biology Society*, (1993),1203-1204.

Grill, W. M., et al., "Deep brain stimulation creates an informational lesion of the stimulated nucleus", *Neuroreport.*, 15(7), (May 19, 2004),1137-40.

Grill, W M., et al., "Electrical properties of implant encapsulation tissue", *Ann Biomed Eng.*, vol. 22, (1994),23-33.

Grill, W M., "Modeling the effects of electric fields on nerve fibers: influence of tissue electrical properties", *IEEE Transactions on Biomedical Engineering*, 46(8), (1999),918-928.

Grill, W. M., et al., "Neural and connective tissue response to long-term implantation of multiple contact nerve cuff electrodes", *J Biomed Mater Res.*, 50(2), (May 2000),215-26.

Grill, W. M., "Neural modeling in neuromuscular and rehabilitation research", *Proceedings of the 23rd Annual International Conference of the IEEE Engineering in Medicine and Biology Society*, vol. 4, (2001),4065-4068.

Grill, W. M., et al., "Non-invasive measurement of the input-output properties of peripheral nerve stimulating electrodes", *Journal of Neuroscience Methods*, 65(1), Mar. 1996,43-50.

Grill, W. M., et al., "Quantification of recruitment properties of multiple contact cuff electrodes", *IEEE Transactions on Rehabilitation Engineering*, [see also *IEEE Trans. on Neural Systems and Rehabilitation*], 4(2), (Jun. 1996),49-62.

Grill, W. M., "Spatially selective activation of peripheral nerve for neuroprosthetic applications", *Ph.D, Case Western Reserve University*, (1995),245 pages.

Grill, W. M., "Stability of the input-output properties of chronically implanted multiple contact nerve cuff stimulating electrodes", *IEEE Transactions on Rehabilitation Engineering* [see also *IEEE Trans. on Neural Systems and Rehabilitation*], (1998),364-373.

Grill, W. M., "Stimulus waveforms for selective neural stimulation", *IEEE Engineering in Medicine and Biology Magazine*, 14(4), (Jul.-Aug. 1995),375-385.

Grill, W. M., et al., "Temporal stability of nerve cuff electrode recruitment properties", *IEEE 17th Annual Conference Engineering in Medicine and Biology Society*, vol. 2, (1995),1089-1090.

Gross, R E., et al., "Advances in neurostimulation for movement disorders", *Neurol Res.*, 22(3), (Apr. 2000),247-258.

Haberler, C , et al., "No tissue damage by chronic deep brain stimulation in Parkinson's disease", *Ann Neurol.*, 48(3), (Sep. 2000),372-376.

Haiying, L., et al., "Intra-operative MR-guided DBS implantation for treating PD and ET", *Proceedings of SPIE* vol. 4319, Department of Radiology & Neurosurgery, University of Minnesota, Minneapolis, MN 55455,(2001),272-276.

Hamel, W , et al., "Deep brain stimulation of the subthalamic nucleus in Parkinson's disease: evaluation of active electrode contacts", *J Neurol. Neurosurg Psychiatry*, 74(8), (Aug. 2003),1036-1046.

Hardman, C. D., et al., "Comparison of the basal ganglia in rats, marmosets, macaques, baboons, and humans: volume and neuronal number for the output, internal relay, and striatal modulating nuclei", *J Comp Neurol.*, 445(3), (Apr. 8, 2002),238-55.

Hashimoto, T. , et al., "Stimulation of the subthalamic nucleus changes the firing pattern of pallidal neurons", *J Neurosci.*, 23(5), (Mar. 1, 2003),1916-23.

Haslinger, B. , et al., "Frequency-correlated decreases of motor cortex activity associated with subthalamic nucleus stimulation in Parkinson's disease.", *Neuroimage*, 28(3), (Nov. 15, 2005),598-606.

Haueisen, J , et al., "The influence of brain tissue anisotropy on human EEG and MEG", *Neuroimage*, 15(1), (Jan. 2002),159-166.

Hemm, S. , et al., "Deep brain stimulation in movement disorders: stereotactic coregistration of two-dimensional electrical field modeling and magnetic resonance imaging.", *J Neurosurg.*, 103(6):, (Dec. 2005),949-55.

Hemm, S. , et al., "Evolution of Brain Impedance in Dystonic Patients Treated by GPi Electrical Stimulation", *Neuromodulation*, 7(2), (Apr. 2004),67-75.

Hershey, T. , et al., "Cortical and subcortical blood flow effects of subthalamic nucleus stimulation in PD.", *Neurology*, 61(6), (Sep. 23, 2003),816-21.

Herzog, J., et al., "Most effective stimulation site in subthalamic deep brain stimulation for Parkinson's disease", *Mov Disord.*, 19(9), (Sep. 2004),1050-4.

Hines, M. L., et al., "The Neuron simulation environment", *Neural Comput.*, 9(6), (Aug. 15, 1997),1179-209.

Hodaie, M , et al., "Chronic anterior thalamus stimulation for intractable epilepsy", *Epilepsia*, 43(6), (Jun. 2002),603-608.

Hoekema, R. , et al., "Multigrid solution of the potential field in modeling electrical nerve stimulation", *Comput Biomed Res.*, 31(5), (Oct. 1998),348-62.

Holsheimer, J. , et al., "Chronaxie calculated from current-duration and voltage-duration data", *J Neurosci Methods*, 97(1), (Apr. 1, 2000),45-50.

Holsheimer, J. , et al., "Identification of the target neuronal elements in electrical deep brain stimulation", *Eur J Neurosci.*, 12(12), (Dec. 2000),4573-7.

Jezernik, S. , et al., "Neural network classification of nerve activity recorded in a mixed nerve", *Neurol Res.*, 23(5), (Jul. 2001),429-34.

Johnson, M. D., et al., "Repeated voltage biasing improves unit recordings by reducing resistive tissue impedances", *IEEE Transactions on Neural Systems and Rehabilitation Engineering*, [see also *IEEE Trans. on Rehabilitation Engineering*], (2005),160-165.

Jones, D K., et al., "Optimal strategies for measuring diffusion in anisotropic systems by magnetic resonance imaging", *Magn. Reson. Med.*, 42(3), (Sep. 1999),515-525.

Kitagawa, M. , et al., "Two-year follow-up of chronic stimulation of the posterior subthalamic white matter for tremor-dominant Parkinson's disease.", *Neurosurgery*, 56(2), (Feb. 2005),281-9.

Krack, P , et al., "Postoperative management of subthalamic nucleus stimulation for Parkinson's disease", *Mov. Disord.*, vol. 17(suppl 3), (2002),188-197.

Le Bihan, D , et al., "Diffusion tensor imaging: concepts and applications", *J Magn Reson Imaging*, 13(4), (Apr. 2001),534-446.

Lee, D C., et al., "Extracellular electrical stimulation of central neurons: quantitative studies", In: *Handbook of neuroprosthetic methods, WE Finn and PG Lopresti (eds) CRC Press*, (2003),95-125.

Levy, A L., et al., "An Internet-connected, patient-specific, deformable brain atlas integrated into a surgical navigation system", *J Digit Imaging*, 10(3 Suppl 1), (Aug. 1997),231-237.

Limousin, P. , et al., "Electrical stimulation of the subthalamic nucleus in advanced Parkinson's disease", *N. Engl J Med.*, 339(16), (Oct. 15, 1998),1105-11.

Mayberg, H. S., et al., "Deep brain stimulation for treatment-resistant depression", *Neuron*, 45(5), (Mar. 3, 2005),651-60.

McIntyre, Cameron C., et al., "Cellular effects of deep brain stimulation: model-based analysis of activation and inhibition",*J Neurophysiol*, 91(4), (Apr. 2004),1457-1469.

McIntyre, Cameron C., et al., "Electric Field and Stimulating Influence generated by Deep Brain Stimulation of the Subthalamaic Nucleus", *Clinical Neurophysiology*, 115(3), (Mar. 2004),589-595.

McIntyre, Cameron C., et al., "Electric field generated by deep brain stimulation of the subthalamic nucleus", *Biomedical Engineering Society Annual Meeting*, Nashville TN, (Oct. 2003).

McIntyre, Cameron C., et al., "Excitation of central nervous system neurons by nonuniform electric fields.", *Biophys. J.*, 76(2), (1999),878-888.

McIntyre, Cameron C., et al., "Extracellular stimulation of central neurons: influence of stimulus waveform and frequency on neuronal output", *J. Neurophysiol.*, 88(4), (Oct. 2002),1592-1604.

McIntyre, Cameron , et al., "Finite element analysis of the current-density and electric field generated by metal microelectrodes", *Ann Biomed Eng.*, 29(3), (2001),227-235.

(56) References Cited

OTHER PUBLICATIONS

McIntyre, C. C., et al., "How does deep brain stimulation work? Present understanding and future questions.", *J Clin Neurophysiol.*, 21(1), (Jan.-Feb. 2004),40-50.

McIntyre, C. C., et al., "Microstimulation of spinal motoneurons: a model study",*Proceedings of the 19th Annual International Conference of the IEEE Engineering in Medicine and Biology society*, vol. 5, (1997),2032-2034.

McIntyre, Cameron C., et al., "Model-based Analysis of deep brain stimulation of the thalamus", *Proceedings of the Second joint EMBS/BMES Conference*, vol. 3, Annual Fall Meeting of the Biomedical Engineering Society (Cat. No. 02CH37392) IEEE Piscataway, NJ,,(2002),2047-2048.

McIntyre, C. C., et al., "Model-based design of stimulus trains for selective microstimulation of targeted neuronal populations", *Proceedings of the 23rd Annual International Conference of the IEEE Engineering in Medicine and Biology Society*, vol. 1, (2001),806-809.

McIntyre, C. C., et al., "Model-based design of stimulus waveforms for selective microstimulation in the central nervous system", *Proceedings of the First Joint [Engineering in Medicine and Biology, 1999. 21st Annual Conf. and the 1999 Annual Fall Meeting of the Biomedical Engineering Soc.] BMES/EMBS Conference*, vol. 1, (1999),384.

McIntyre, Cameron C., et al., "Modeling the excitability of mammalian nerve fibers: influence of afterpotentials on the recovery cycle", *J Neurophysiol*, 87(2), (Feb. 2002),995-1006.

McIntyre, Cameron C., et al., "Selective microstimulation of central nervous system neurons", *Annals of biomedical engineering.*, 28(3), (Mar. 2000),219-233.

McIntyre, C. C., et al., "Sensitivity analysis of a model of mammalian neural membrane", *Biol Cybern.*, 79(1), (Jul. 1998),29-37.

McIntyre, Cameron C., et al., "Uncovering the mechanism(s) of action of deep brain stimulation: activation, inhibition, or both.", *Clin Neurophysiol*, 115(6), (Jun. 2004),1239-48.

McIntyre, Cameron C., et al., "Uncovering the mechanisms of deep brain stimulation for Parkinson's disease through functional imaging, neural recording, and neural modelling", *Crit Rev Biomed Eng.*, 30(4-6), (2002),249-281.

McNeal, D R., et al., "Analysis of a model for excitation of myelinated nerve", *IEEE Trans Biomed Eng.*, vol. 23, (1976),329-337.

Merrill, D. R., et al., "Electrical stimulation of excitable tissue: design of efficacious and safe protocols", *J Neurosci Methods*, 141(2), (Feb. 15, 2005),171-98.

Micheli-Tzanakou, E. , et al., "Computational Intelligence for target assesment in Parkinson's disease", *Proceedings of SPIE* vol. 4479, Applications and Science of Neural Networks, Fuzzy Systems, and Evolutionary Computation IV,(2001),54-69.

Miocinovic, S. , et al., "Computational analysis of subthalamic nucleus and tenticular fasciculus activation during therapeutic deep brain stimulation.", *J Neurophysiol.*, 96(3), (Sep. 2006),1569-80.

Miocinovic, S. , et al., "Sensitivity of temporal excitation properties to the neuronal element activated by extracellular stimulation", *J Neurosci Methods*, 132(1), (Jan. 15, 2004),91-9.

Miranda, P. C., et al., "The distribution of currents inducedin the brain by Magnetic Stimulation: a finite element analysis incorporating DT-MRI-derived conductivity data", *Proc. Intl. Soc. Mag. Reson. Med.* 9, (2001),1540.

Miranda, P. C., et al., "The Electric Field Induced in the Brain by Magnetic Stimulation: A 3-D Finite-Element Analysis of the Effect of Tissue Heterogeneity and Anisotropy", *IEEE Transactions on Biomedical Enginering*, 50(9), (Sep. 2003),1074-1085.

Moffitt, M A., et al., "Prediction of myelinated nerve fiber stimulation thresholds: limitations of linear models", *IEEE Transactions on Biomedical Engineering*, 51(2), (2003),229-236.

Montgomery, E. B., et al., "Mechanisms of deep brain stimulation and future technical developments.", *Neurol Res.*, 22(3), (Apr. 2000),259-66.

Moro, E , et al., "The impact on Parkinson's disease of electrical parameter settings in STN stimulation", *Neurology*, 59(5), (Sep. 10, 2002),706-703.

Moss, J. , et al., "Electron microscopy of tissue adherent to explanted electrodes in dystonia and Parkinson's disease", *Brain*, 127(Pt 12), (Dec. 2004),2755-63.

Nowak, L G., et al., "Axons, but not cell bodies, are activated by electrical stimulation in cortical gray matter. I. Evidence from chronaxie measurements", *Exp. Brain Res.*, 118(4), (Feb. 1998),477-488.

Nowak, L G., et al., "Axons, but not cell bodies, are activated by electrical stimulation in cortical gray matter. II. Evidence from selective inactivation of cell bodies and axon initial segments", *Exp. Brain Res.*, 118(4), (Feb. 1998),489-500.

Nowinski, W. L., et al., "Statistical analysis of 168 bilateral subthalamic nucleus implantations by means of the probabilistic functional atlas.", *Neurosurgery*, 57(4 Suppl), (Oct. 2005),319-30.

O'Suilleabhain, P E., et al., "Tremor response to polarity, voltage, pulsewidth and frequency of thalamic stimulation", *Neurology*, 60(5), (Mar. 11, 2003),786-790.

Obeso, J. A., et al., "Deep-brain stimulation of the subthalamic nucleus or the pars interna of the globus pallidus in Parkinson's disease.", *N. Engl J Med.*, 345(13), The Deep-Brain Stimulation for Parkinson's Disease Study Group,(Sep. 27, 2001),956-63.

Patrick, S. K., et al., "Quantification of the UPDRS rigidity scale", *IEEE Transactions on Neural Systems and Rehabilitation Engineering*, [see also *IEEE Trans. on Rehabilitation Engineering*], 9(1), (2001),31-41.

Phillips, M. D., et al., "Parkinson disease: pattern of functional MR imaging activation during deep brain stimulation of subthalamic nucleus—initial experience", *Radiology*, 239(1), (Apr. 2006),209-16.

Pierpaoli, C , et al., "Toward a quantitative assessment of diffusion anisotropy",*Magn Reson Med.*, 36(6), (Dec. 1996),893-906.

Plaha, P. , et al., "Stimulation of the caudal zona incerta is superior to stimulation of the subthalamic nucleus in improving contralateral parkinsonism.", *Brain*, 129(Pt 7), (Jul. 2006),1732-47.

Plonsey, R , et al., "Considerations of quasi-stationarity in electrophysiological systems", *Bull Math Biophys.*, 29(4), (Dec. 1967),657-664.

Ranck, J B., "Specific impedance of rabbit cerebral cortex.", *Exp. Neurol.*, vol. 7, (Feb. 1963),144-152.

Ranck, J B., et al., "The Specific impedance of the dorsal columns of the cat: an anisotropic medium", *Exp. Neurol.*, 11, (Apr. 1965),451-463.

Ranck, J B., "Which elements are excited in electrical stimulation of mammalian central nervous system: a review", *Brain Res.*, 98(3), (Nov. 21, 1975),417-440.

Rattay, F. , et al., "A model of the electrically excited human cochlear neuron. I. Contribution of neural substructures to the generation and propagation of spikes", *Hear Res.*, 153(1-2), (Mar. 2001),43-63.

Rattay, F. , "A model of the electrically excited human cochlear neuron. II. Influence of the three-dimensional cochlear structure on neural excitability", *Hear Res.*, 153(1-2), (Mar. 2001),64-79.

Rattay, F , "Analysis of models for external stimulation of axons", *IEEE Trans. Biomed. Eng.*, vol. 33, (1986),974-977.

Rattay, F. , "Analysis of the electrical excitation of CNS neurons", *IEEE Transactions on Biomedical Engineering*, 45(6), (Jun. 1998),766-772.

Rattay, F. , "Arrival at Functional Electrostimulation by modelling of fiber excitation", *Proceedings of the Ninth annual Conference of the IEEE Engineering in Medicine and Biology Society*, (1987),1459-1460.

Rattay, F. , "The influence of intrinsic noise can preserve the temporal fine structure of speech signals in models of electrically stimulated human cochlear neurones", *Journal of Physiology*, Scientific Meeting of the Physiological Society, London, England, UK Apr. 19-21, 1999,(Jul. 1999),170P.

Rizzone, M , et al., "Deep brain stimulation of the subthalamic nucleus in Parkinson's disease: effects of variation in stimulation parameters", *J. Neurol. Neurosurg. Psychiatry.*, 71(2), (Aug. 2001),215-219.

(56) References Cited

OTHER PUBLICATIONS

Rose, T. L., et al., "Electrical stimulation with Pt electrodes. VIII. Electrochemically safe charge injection limits with 0.2 ms pulses [neuronal application]", *IEEE Transactions on Biomedical Engineering*, 37(11), (Nov. 1990),1118-1120.

Rubinstein, J. T., et al., "Signal coding in cochlear implants: exploiting stochastic effects of electrical stimulation", *Ann Otol Rhinol Laryngol Suppl.*, 191, (Sep. 2003),14-9.

Saint-Cyr, J A., et al., "Localization of clinically effective stimulating electrodes in the human subthalamic nucleus on magnetic resonance imaging", *J. Neurosurg.*, 87(5), (Nov. 2002),1152-1166.

Sances, A , et al., "In Electroanesthesia: Biomedical and Biophysical Studies", *A Sances and SJ Larson, Eds., Academic Press*, NY, (1975),114-124.

Schwan, H. P., et al., "The conductivity of living tissues.", *Ann N Y Acad Sci.*, 65(6), (Aug. 1957),1007-13.

St. Jean, P , et al., "Automated atlas integration and interactive three-dimensional visualization tools for planning and guidance in functional neurosurgery", *IEEE Transactions on Medical Imaging*, 17(5), (1998),672-680.

Starr, P A., et al., "Implantation of deep brain stimulators into the subthalamic nucleus: technical approach and magnetic resonance imaging-verified lead locations", *J. Neurosurg.*, 97(2), (Aug. 2002),370-387.

Sterio, D , et al., "Neurophysiological refinement of subthalamic nucleus targeting", *Neurosurgery*, 50(1), (Jan. 2002),58-67.

Struijk, J. J., et al., "Excitation of dorsal root fibers in spinal cord stimulation: a theoretical study", *IEEE Transactions on Biomedical Engineering*, 40(7), (Jul. 1993),632-639.

Struijk, J J., et al., "Recruitment of dorsal column fibers in spinal cord stimulation: influence of collateral branching", *IEEE Transactions on Biomedical Engineering*, 39(9), (Sep. 1992),903-912.

Tamma, F , et al., "Anatomo-clinical correlation of intraoperative stimulation-induced side-effects during HF-DBS of the subthalamic nucleus", *Neurol Sci.*, vol. 23 (Suppl 2), (2002),109-110.

Tarler, M. , et al., "Comparison between monopolar and tripolar configurations in chronically implanted nerve cuff electrodes", *IEEE 17th Annual Conference Engineering in Medicine and Biology Society*, vol. 2, (1995),1093-1094.

Taylor, R. S., et al., "Spinal cord stimulation for chronic back and leg pain and failed back surgery syndrome: a systematic review and analysis of prognostic factors", *Spine*, 30(1), (Jan. 1, 2005),152-60.

Testerman, Roy L., "Coritical response to callosal stimulation: A model for determining safe and efficient stimulus parameters", *Annals of Biomedical Engineering*, 6(4, (1978),438-452.

Trost, M. , et al., "Network modulation by the subthalamic nucleus in the treatment of Parkinson's disease", *Neuroimage*, 31(1), (May 15, 2006),301-7.

Tuch, D S., et al., "Conductivity mapping of biological tissue using diffusion MRI.", *Ann N Y Acad Sci.*, 888, (Oct. 30, 1999),314-316.

Tuch, D S., et al., "Conductivity tensor mapping of the human brain using diffusion tensor MRI", *Proc Natl Acad Sci U S A.*, 98(20), (Sep. 25, 2001),11697-11701.

Tyler, R. S., et al., "Update on bilateral cochlear implantation", *Curr Opin. Otolaryngol Head Neck Surg.*, 11(5), (Oct. 2003),388-93.

Veraart, C. , et al., "Selective control of muscle activation with a multipolar nerve cuff electrode", *IEEE Transactions on Biomedical Engineering*, 40(7), (Jul. 1993),640-653.

Vercueil, L , et al, "Deep brain stimulation in the treatment of severe dystonia",*J. Neurol.*, 248(8), (Aug. 2001),695-700.

Vidailhet, M. , et al., "Bilateral deep-brain stimulation of the globus pallidus in primary generalized dystonia", *N Engl J Med.*, 352(5), (Feb. 3, 2005),459-67.

Viola, P. , et al., "Alignment by maximization of mutual information", *International Journal of Computer Vision*, 24(2), (1997),137-154.

Vitek, J L., "Mechanisms of deep brain stimulation: excitation or inhibition", *Mov. Disord.*, vol. 17 (Suppl. 3), (2002),69-72.

Voges, J , et al., "Bilateral high-frequency stimulation in the subthalamic nucleus for the treatment of Parkinson disease: correlation of therapeutic effect with anatomical electrode position", *J. Neurosurg.*, 96(2), (Feb. 2002),269-279.

Volkmann, J. , et al., "Basic algorithms for the programming of deep brain stimulation in Parkinson's disease", *Mov Disord.*, 21 Suppl 14, (Jun. 2006),S284-9.

Volkmann, J , et al., "Introduction to the programming of deep brain stimulators", *Mov. Disord.*, vol. 17 (Suppl 3), (2002),181-187.

Wakana, S , et al., "Fiber tract-based atlas of human white matter anatomy", *Radiology*, 230(1), (Jan. 2004),77-87.

Walter, B. L., et al., "Surgical treatment for Parkinson's disease", *Lancet Neurol.*, 3(12), (Dec. 2004),719-28.

Warman, E N., et al., "Modeling the effects of electric fields on nerve fibers: Determination of excitation thresholds", *IEEE Transactions on Biomedical Engineering*, 39(12), (1992),1244-1254.

Wei, X. F., et al., "Current density distributions, field distributions and impedance analysis of segmented deep brain stimulation electrodes", *J Neural Eng.*, 2(4), (Dec. 2005),139-47.

Wu, Y R., et al., "Does Stimulation of the GPi control dyskinesia by activating inhibitory axons?", *Mov. Disord.*, vol. 16, (2001),208-216.

Yelnik, J , et al., "Localization of stimulating electrodes in patients with Parkinson disease by using a three-dimensional atlas-magnetic resonance imaging coregistration method", *J Neurosurg.*, 99(1), (Jul. 2003),89-99.

Yianni, John , et al., "Globus pallidus internus deep brain stimulation for dystonic conditions: a prospective audit", *Mov. Disord.*, vol. 18, (2003),436-442.

Zonenshayn, M , et al., "Comparison of anatomic and neurophysiological methods for subthalamic nucleus targeting", *Neurosurgery*, 47(2), (Aug. 2000),282-292.

Zonenshayn, M. , et al., "Location of the active contact within the subthalamic nucleus (STN) in the treatment of idiopathic Parkinson's disease.", *Surg Neurol.*, 62(3), (Sep. 2004),216-25.

* cited by examiner

SYSTEMS AND METHODS FOR DETERMINING VOLUME OF ACTIVATION FOR SPINAL CORD AND PERIPHERAL NERVE STIMULATION

CROSS-REFERENCE TO RELATED PATENT DOCUMENTS

This application is a continuation-in-part of U.S. application Ser. No. 11/715,829, filed on Mar. 8, 2007, now U.S. Pat. No. 8,810,601 which claims the benefit of priority, under 35 U.S.C. Section 119(e), to U.S. Provisional Patent Application Ser. No. 60/743,445, filed on Mar. 9, 2006, both of which are incorporated by reference herein.

GOVERNMENT INTEREST

The subject matter described herein was made with support from the U.S. Government under funding provided by National Institutes of Health (NIH) Grant Numbers NS-50449 and NS-52042. The United States Government may have certain rights to the invention.

TECHNICAL FIELD

This patent application pertains generally to neurosurgery and more particularly, but not by way of limitation, to systems and methods for determining a volume of activation, such as for deep brain stimulation (DBS), spinal cord stimulation (SCS) and peripheral nerve stimulation.

BACKGROUND

Deep brain stimulation (DBS) and other forms of neuromodulation, such as spinal cord stimulation (SCS) and peripheral nerve stimulation (PNS), have rapidly emerged as effective clinical treatments, such as for movement disorders, thereby revolutionizing the field of functional neurosurgery and virtually replacing tissue ablation for the treatment of medically refractory movement disorders. However, little is known about the neural response, or therapeutic mechanisms of the stimulation. The subthalamic nucleus (STN) represents a target for DBS electrodes. However, the STN is a small nucleus surrounded by a variety of fiber tracts, many of which are responsible for stimulation-induced side effects.

OVERVIEW

The present inventors have recognized that there exists a significant need to characterize the effects of DBS and other forms of neuromodulation, such as spinal cord stimulation and peripheral nerve stimulation, on the underlying neural tissue and to improve or optimize electrode design to enhance the therapeutic effectiveness of DBS and other forms of neuromodulation. These procedures represent a therapy for essential tremor, Parkinson's disease, dystonia, other movement disorders, and other disorders. In addition, DBS and other forms of neuromodulation may be useful in the treatment of epilepsy, obsessive-compulsive disorder, and depression. For example, spinal cord and peripheral nerve stimulation is used for treating chronic pain and vagal nerve stimulation is used as an adjunct therapy for epilepsy and major depression. However, the understanding of the neural effects of DBS and other forms of neuromodulation are limited, and significant opportunities exist to improve or optimize electrode design to enhance therapeutic effectiveness.

To address these issues, we have developed computational tools, such as to predict the neural response to stimulation.

In an illustrative example, electrostatic approximation can be applied in neural stimulation modeling by treating the electrode as a perfect current source and the neural tissue as a purely conductive medium. However, clinical DBS amd SCS electrodes are typically voltage controlled, use an asymmetrical biphasic stimulus waveform, and are generally surrounded by a three-dimensional (3D) anisotropic inhomogeneous tissue medium. Failing to account for these conditions can lead to overestimating the volume of activation (VOA) (e.g., by ~30%) compared to voltage-controlled stimulation for typical therapeutic stimulation parameter settings. This overestimation is generally directly related to the electrode capacitance and the stimulation pulse width. Thus, there exists a need, among other things; to accurately predict the effects of DBS and other forms of neuromodulation such as spinal cord stimulation.

To more accurately model DBS, spinal cord, and peripheral nerve stimulation, for example, the present inventors have developed, among other things, a finite element model (FEM) of the electrode and tissue medium. A Fourier FEM solver determines the potential distribution in the tissue in time and space concurrently. In certain examples, electric field data from the determined potential distribution can be coupled to a multi-compartment neuron model to predict neural activation, or determined extracellular voltages can be applied to detailed multi-compartment cable models of myelinated axons to determine neural activation. Generally, neural activation volumes can be calculated as a function of one or more stimulation parameters and a magnitude of one or more capacitive components of the tissue-electrode interface.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one, regardless of other instances where "one or more" or "at least one" are recited. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

1. Deep Brain Stimulation of the Subthalamic Nucleus: Model-Based Analysis of the Effects of Electrode Capacitance on the Volume of Activation A. Introduction Generally, a first step toward understanding the effects of deep brain stimulation (DBS) or other forms of neuromodulation, like spinal cord stimulation (SCS) and peripheral nerve stimulation includes characterizing the electric field and volume of tissue activated by the stimulation. The electric field is typically dependent on the shape of the electrode and the electrical conductivity properties of the tissue medium. In addition, when using a voltage-controlled stimulation (as can be the case with certain clinical DBS systems), the electrode capacitance can substantially affect the time course and amplitude of the stimulus waveform. As such, the present inventors have developed, among other things, a DBS neuromodulation modeling system that, in certain examples, can integrate time dependent components of an applied electric field and the three-dimensionally complex anisotropy and inhomogeneity of the tissue electrical properties to predict the volume of activation (VOA) as a function of the stimulation parameters.

Figure 1:
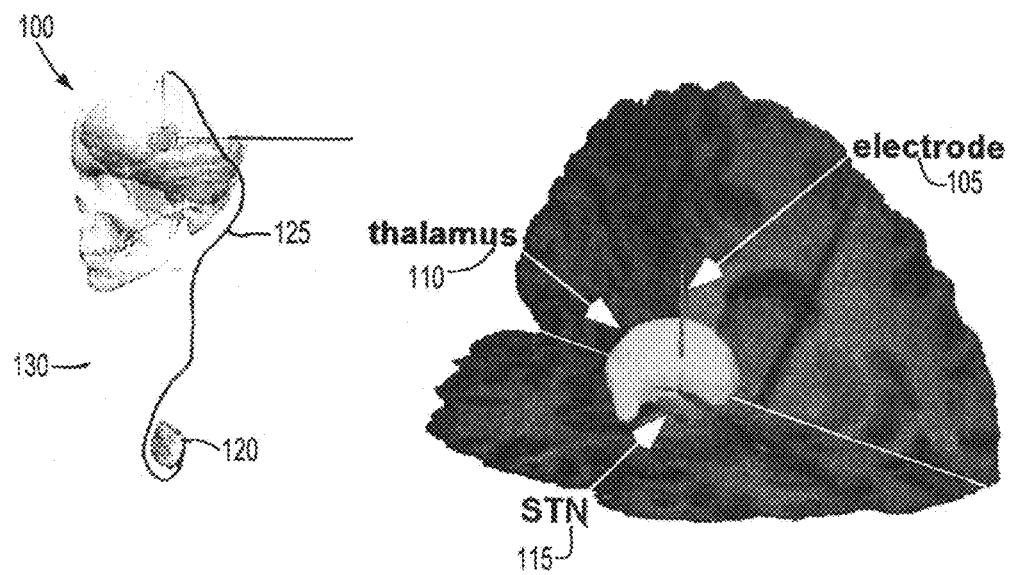
FIG. 1 illustrates generally an example of a system including an implanted electrode, a leadwire, and an implantable pulse generator (IPG).

FIG. 1 illustrates generally an example of portions of a system 100 including an implanted electrode 105, a leadwire 125, and an implantable pulse generator (IPG) 120. Generally, the system 100 can be configured to deliver DBS or other forms of neuromodulation. In an example, the implanted electrode can include an implanted quadrapolar electrode. In this example, the implanted electrode is configured to provide ongoing or continuous high frequency stimulation to the subthalamic nucleus (STN) 115 of the brain. In the example of FIG. 1, the STN 115 is shown in relation to the thalamus 110, both of which are part of a diencephalon region of the brain. The electrode could also be used to provide stimulation to the spinal cord or a peripheral nerve.

Figure 2:
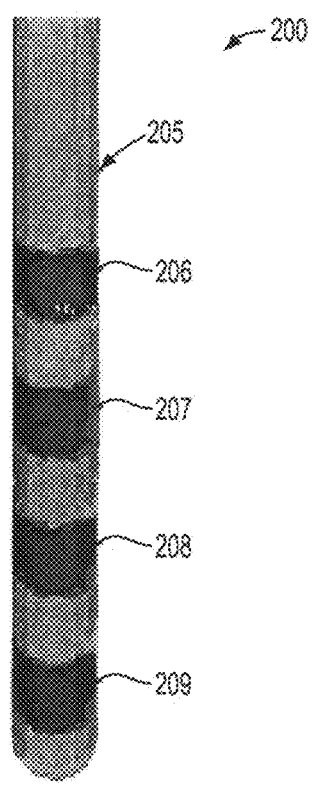
FIG. 2 illustrates generally an example of a system including an implantable electrode having at least one contact.

FIG. 2 illustrates generally an example of portions of a system 200 including an implantable electrode 205 having at least one contact 206-209. In this example, the implanted electrode 205 includes a most proximal first contact 206, a second contact 207, a third contact 208, and a most distal fourth contact 209. In other examples, the implanted electrode 205 can include more (e.g., five, six, etc.) or less (e.g., one, two, or three) contacts. In an example, the implanted electrode 205 can include a DBS lead, such as the Medtronic 3387-89 DBS lead (Medtronic, Inc., Minneapolis, Minn.).

Figure 3:
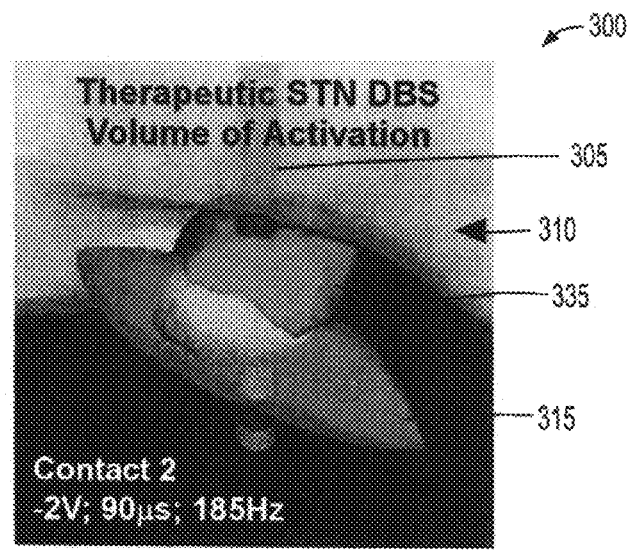
FIG. 3 illustrates generally an example of an illustration including a predicted volume of tissue activated, or VOA, as a function of the stimulation parameters and the position of the implanted electrode in the tissue medium.

FIG. 3 illustrates generally an example of an illustration 300 including a predicted volume of tissue activated, or VOA, 335 as a function of the stimulation parameters and the position of the implanted electrode 305 in the tissue medium (e.g., the nervous tissue of the brain). The tissue medium can be neural tissue in the brain or other part of the central nervous system, such as the spinal cord. The neural tissue can also be part of the peripheral nervous system such as the somatic and autonomic nervous system. For example, target sites of the peripheral nervous system for which a VOA can be predicted and for which other methods of the present invention can be utilized include cranial nerves (such as, for example, the vagus nerve and/or sacral nerve) and spinal nerves. Target sites in the autonomic nervous system include the sympathetic nervous system and parasympathetic nervous system. Specific sites within these systems include sympathetic or parasympathetic nerves or ganglia.

The methods can also be used to determine treatment for stroke patients, patients suffering from traumatic brain injury or movement disorders. For example, methods of the present invention can be used to determine electrical stimulation of the cerebellum, such as the cerebellar dentate nucleus or the corpus callosum to enhance motor and cognitive recovery following stroke, such as ischemic stroke. Methods can also be used to determine electrical stimulation of the intralaminar nuclei (of the thalamus) for enhancing motor, arousal and cognitive function following traumatic brain injury. Methods can also be used to determine electrical stimulation of the anterior nucleus of the thalamus for epilepsy; the nucleus accumbens and area 25 for depression; the subthalamic nucleus and globus pallidus internus for movement disorders such as Parkinson's Disease, tremors or dystonia; and the VIM for essential tremor.

In this example, the implanted electrode 305 is positioned to provide stimulation to the STN 315, which lies beneath the thalamus 310. In the example of FIG. 3, the VOA was calculated as a function of a stimulation having the following stimulation parameters: a voltage of −2V, a pulse width of 90 μs, and a stimulation frequency of 185 Hz. In other examples, other stimulation parameters can be used.

B. Exemplary Methods

In an example, neural stimulation was estimated with an integrated computer model that combined a finite-element based electric field solution with a multi-compartment cable model of myelinated axons. In this example, the Poisson equation was solved to determine voltage within the tissue medium and then interpolated onto cable model neurons. The cable models were used to define threshold values of the stimulation voltage for generating action potentials. Then, activating function values were determined from a second difference of the voltage solution at the stimulation threshold for each axon at the site of action potential initiation. Finally, in this example, the activating function values were coupled to an analytical function, providing a spatial map for predicting VOA, which can be displayed to a clinical user.

Figure 4:
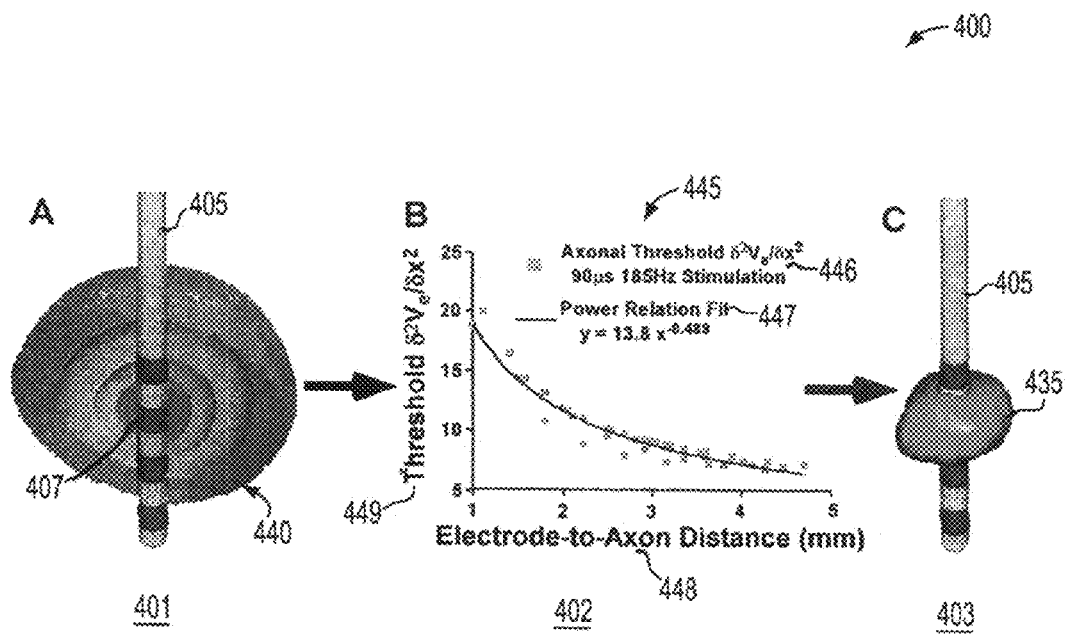
FIG. 4 illustrates generally an example of a method including calculating a VOA.

FIG. 4 illustrates generally an example of a method 400 including calculating a VOA 435. At 401, a potential distribution 440 was generated by the FEM for a stimulation having stimulation parameters of: a voltage of −1V, a pulse width of 90 μs, and a stimulation frequency of 185 Hz delivered at a second contact 407 of an electrode 405.

At 402, an activating function relationship 445 was determined. The activating function relationship 445 displays activating function values 446 and a resulting power relation (or other) fit 447 as a function of a threshold (characterized by the relationship $$\frac{\delta^2 V_e}{\delta x^2}\Big)$$

449 on a y-axis and an electrode-to-axon distance (mm) 448 on the x-axis. In this example, the activating function values 446 were determined for fifty 5.7 μm diameter myelinated axon models randomly distributed around the electrode 405. In this example, the power relation fit 447 is characterized by the line $y=13.6x^{-0.489}$ At 403, the activating function values 446 were coupled to an analytical function (e.g., a bioelectric field solver, such as BioPSE (Scientific Computing and Imaging Institute)) that provided a predicted spatial map for the VOA 435 using information from the activating function relationship 445.

In an example, three-dimensionally complex tissue anisotropy and inhomogeneity can be incorporated into the computer-implemented model, such as by using conductivity tensors, which can be derived from human diffusion tensor magnetic resonance images (DTI) of the STN and surrounding structures as well as the spinal cord.

Figure 5:
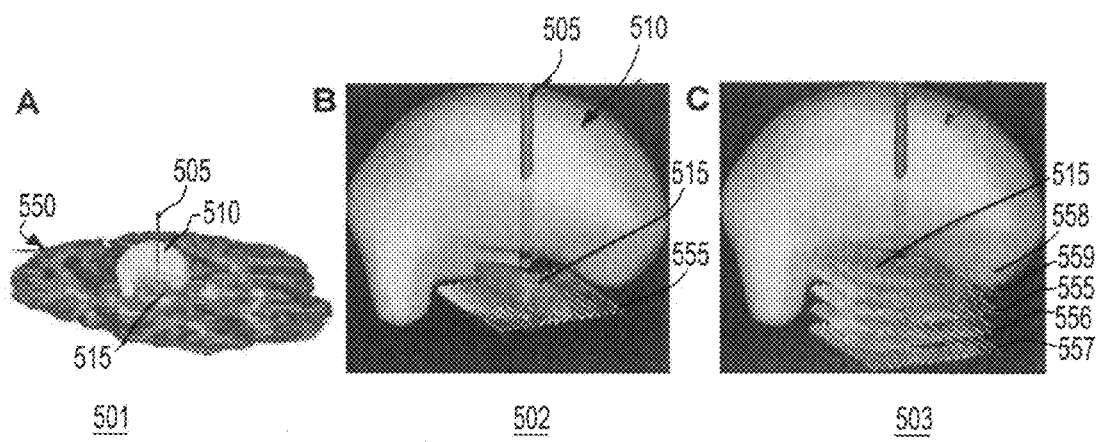
FIG. 5 illustrates generally an example of a model including an electrical model of STN DBS.

FIG. 5 illustrates generally an example of a model 500 including an electrical model of STN DBS. At 501, an axial slice of the DTI 550 is shown co-registered with an electrode 505 and anatomical volumes of the thalamus 510 and STN 515. In this example, the color coding of the axial slice of the DTI 550 represents fractional anisotropy (FA), the red representing a high degree of anisotropy and, the color spectrum correlative to the degree of anisotropy, the blue representing a low degree of anisotropy.

At 502, the anatomical volumes of the thalamus 510 and the STN 5150 are shown co-registered with the electrode 505 and a first selected region of conductivity tensors 555.

At 503, the electrode 505 is shown surrounded by a set of selected regions of conductivity tensors 555-559, representing a highly complex 3D anisotropic and inhomogeneous tissue medium.

In an example, a Fourier FEM can separate the stimulus waveform into component frequencies, can solve the Poisson equation at a particular component frequency by using a complex stiffness matrix (e.g., that includes a reactive component rather than merely including conductive components), can scale or phase shift the results, and can reassemble the time-dependent solution.

Figure 6:
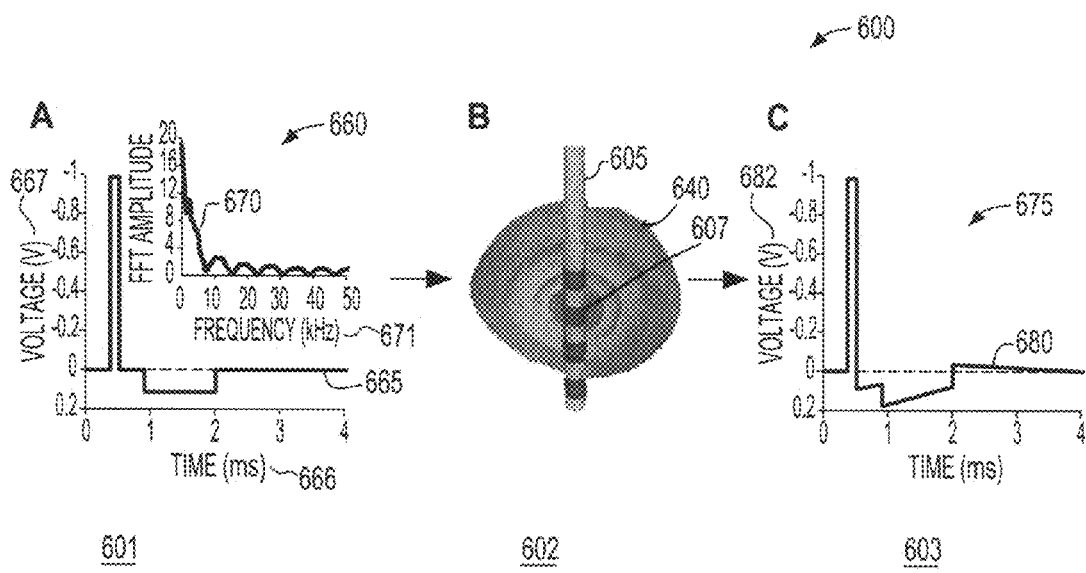
FIG. 6 illustrates generally an example of a method including using the Fourier FEM to calculate the voltage in the tissue.

FIG. 6 illustrates generally an example of a method 600 including using the Fourier FEM to calculate the voltage in the tissue. At 601, the relationship 660 can be recorded. The relationship 660 includes a stimulation waveform 665, shown in relation to time (ms) 666 and voltage (V) 667, recorded from an implantable pulse generator (IPG) (such as the IPG 120), the stimulation having the following stimulation parameters: a voltage of −1V, a 210 µs pulse width, and a stimulation frequency of 185 Hz. A waveform 670, inset in the relationship 660 and shown in relation to frequency (kHz) 671 and FFT amplitude 672, shows the Fourier transform of the stimulation waveform 665 into the frequency domain.

At 602, the FEM can be solved using a computer, providing a potential distribution 640 as a function of space at each frequency component of the solution. An example of the potential distribution 640, at 602, is shown at a second contact 607 of an electrode 605.

At 603, the relationship 675 can be recorded. The relationship 675 includes an FEM waveform 680, shown in relation to time (ms) 681 and voltage (V) 682. In this example, the inverse Fourier transform of the FEM solution generated the stimulation voltage as a function of space and time in the tissue medium surrounding the electrode (e.g., the nervous tissue of the brain, spinal cord, peripheral nerve or other neural tissue).

C. Example of Results

Using the examples of methods discussed above, the present inventors have recognized, among other things, that including capacitive effects of DBS and other forms of neuromodulation can substantially affect the estimated VOA for a stimulation. For example, the present inventors have recognized that electrostatic models of DBS will tend to overestimate VOAs. In certain examples, the amount of error caused by the electrostatic approximation can depend on electrode capacitance or stimulation pulse width. As an illustrative example, suppose that the capacitance of a DBS electrode can be ∼3.3 µF. Further, suppose that a clinically effective stimulus pulse duration can range from 60-450 µs. The largest electrostatic model errors typically occur when using longer pulse widths or smaller electrode capacitance values. Smaller capacitance values can cause the model to have a shorter time constant, which can magnify the amount of the electrostatic error. Additionally, larger electrostatic model errors typically occur when using larger stimulation voltages.

Figure 7:
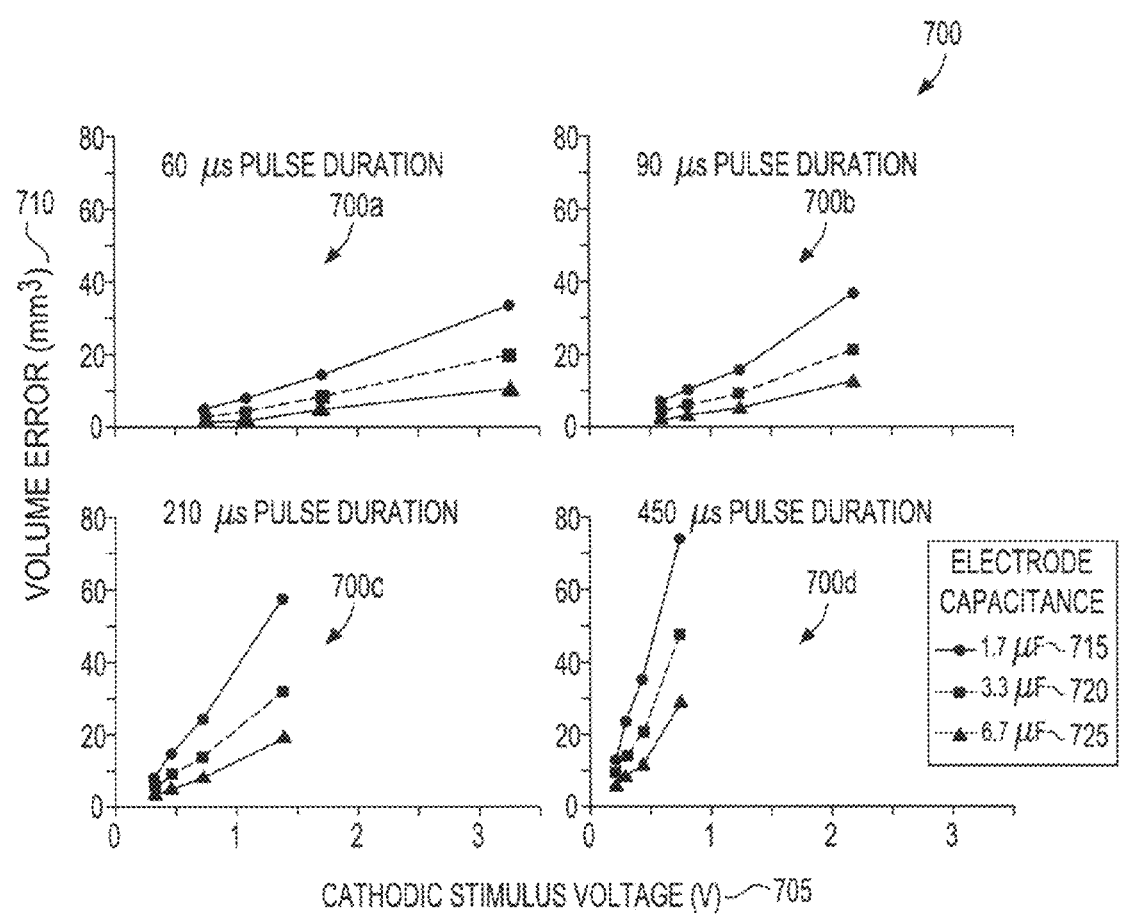
FIG. 7 illustrates generally examples of illustrations including electrostatic model errors.

FIG. 7 illustrates generally examples of illustrations 700 including electrostatic model errors. In this example, illustrations 700a-d include relationships between a 60 µs stimulation pulse, a 90 µs stimulation pulse, a 210 µs stimulation pulse, and a 450 µs stimulation pulse respectively, and a 1.7 µF electrode capacitance 715, a 3.3 µF electrode capacitance 720, and a 6.7 µF electrode capacitance 725 with respect to a cathodic stimulus voltage (V) 705 and a volume error (mm$^3$) 710. In this example, the volume error (mm$^3$) 710 was calculated as the difference between the VOA predicted using the electrostatic FEM and the Fourier FEM. Further, in this example, the electrostatic model always overestimated the VOA. FIG. 7 shows generally that the volume error is at least in part dependent on electrode capacitance, pulse duration, or stimulus voltage.

2. Tissue and Electrode Capacitance Reduce Neural Activation Volumes During Deep Brain Stimulation A. Introduction Generally, theoretical analysis of neural stimulation yields the following: (1) the electric field generated by the stimulation typically depends on the shape of the electrode, the distribution of cathode(s) and anode(s), and the biophysical properties of the tissue medium; and (2) the neural response to the applied electric field is generally related to the second spatial derivative of the extracellular potentials distributed along a neural process.

Certain models of neurostimulation ignore the effects of electrode and tissue capacitance, instead treating the electrode as a perfect voltage or current source and the surrounding tissue as a purely conductive medium (this can be referred to as a quasistatic or electrostatic assumption). The errors induced by this assumption may be significant in certain forms of neurostimulation, such as brain stimulation, where even small changes, e.g. ∼1 mm, in the spread of activation can have dramatic consequences on desired therapeutic effects or on undesired side effects induced by the stimulation. Thus, to quantitatively evaluate the volume of tissue activation (VTA), or VOA, as a function of the stimulation parameters, the present inventors have provided a model that can accurately account for one or more such components of neurostimulation.

Neurostimulation devices can use current-controlled or voltage-controlled pulse generators. In certain examples, such as during reversible (non-faradic) reactions at the electrode-tissue interface, electrode capacitance can influence the electric field transmitted to the tissue during voltage-controlled stimulation and conversely tissue capacitance can influence the electric field transmitted to the tissue during current-controlled stimulation. These reactive components can affect the shape and amplitude of the stimulus waveform delivered to the tissue medium and can modulate the neural response to the applied electric field. Previously ignored, these capacitive components of the electrode-tissue interface may be useful in more accurately estimating the VTA, or VOA.

The present inventors have developed an integrated spatiotemporal model of current-controlled or voltage-controlled neurostimulation, such as in the context of DBS, SCS, PNS, and other forms of neuromodulation, that quantifies the activation of axons surrounding the electrode. Myelinated axons typically represent highly excitable neural elements surrounding an extracellular stimulating electrode. The therapeutic response to DBS is typically linked with axonal activation.

B. Examples of Methods

In an example, determining the role of capacitance on the volume of axonal tissue activated with clinical DBS or other neuromodulation parameters can use a computer model of neurostimulation that integrates finite-element based electric field solutions and multi-compartment cable models of myelinated axons.

In an example, the Poisson equation was solved with the Fourier FEM to determine the voltage distribution in the tissue medium, which was then interpolated onto the model axons. These model axons were used to search for threshold stimulus amplitudes for generating action potentials. This model can be used to predict the individual or combined effect of electrode capacitance and bulk tissue capacitance on neural activation, such as in using DBS electrodes in the context of voltage-controlled or current-controlled stimulation.

i. Fourier FEM

As an illustrative example, axisymmetric finite element models of DBS electrodes were created using multiphysics modeling software (e.g., FEMLAB 3.1 (COMSOL Inc., Burlington, Mass.)). The example of the model included variable resolution meshes of 13,201 nodes for monopolar stimulation and 17,229 nodes for bipolar stimulation. In this example, the axisymmetric volume conductor measured 10 cm tall by 5 cm wide. The tissue medium was at least initially modeled as homogeneous and isotropic with conductivity of 0.3 S/m, a representative value for brain tissue. Other conductivity values could be used in the case of other neural tissue, as shown in Table 1 below:

| Compartmental Conductivities (S/m) | |
| --- | --- |
| gray matter | 0.23 |
| white matter | 0.60 longitudinal |
|  | 0.083 transverse |
| cerebrospinal fluid | 1.7 |
| epidural fat | 0.04 |
| dura matter | 0.03 |
| vertebral bone | 0.02 |
| surrounding layer | 0.004 |
| encapsulation layer | 0.002 |

See Wesselink et al., "Analysis of Current Density and Related Parameters in Spinal Cord Stimulation," *IEEE Transactions on Rehabilitation Engineering*, Vol. 6, No. 2, pp. 200-207 (June 1998), which is incorporated by reference herein.

The electrode geometry was based on the Medtronic 3387-89 DBS electrode having the contact dimensions 1.5 mm height and 1.27 mm diameter. Voltage or current sources were specified at the electrode contact, and the electrode shaft was modeled as an electrical insulator. The Poisson equation was solved using direct matrix inversion (e.g., UMFPACK solver) at various component frequencies of the stimulus waveform to determine the potential distribution ($V_e$) generated within the tissue medium (stiffness matrix $\sigma$), based on a collection of sources (I):

$$\nabla \cdot \sigma \nabla V_e = -I \qquad (\text{Eq. 1})$$

In a monopolar stimulation example, to mimic the effects of an indifferent return electrode, ground nodes were placed around the exterior boundary of the finite element mesh. In a bipolar stimulation example, a second electrode was added with a 1.5 mm gap between contacts and the ground nodes were removed from the exterior boundary of the finite element mesh. Dirichlet and von Neumann boundary conditions can be imposed to control voltage or current values at the electrode surface and to confine current flow to within the finite element model, respectively.

The Fourier FEM can be used to calculate time-dependent and space-dependent voltages within bioelectric volume conductors. This can include four parts for a particular solution (see, e.g., FIG. 8). First, the stimulus waveform to be applied through the electrode contact can be constructed in the time domain. The stimulus can include an arbitrarily complex waveform. Second, the waveform can be converted from the time domain to the frequency domain, such as by using a discrete Fourier transform (DFT). This can be accomplished using simulation software (e.g., Matlab (Mathworks, Natick, Mass.)), which can provide the magnitude and phase of a set of frequency components that correspond to the time domain stimulus. Third, the Poisson equation can be solved at one or all of the frequency components of the DFT, such as by using direct matrix inversion. A Poisson equation with purely conductive elements does not allow reactive components to represent an electrostatic solution. To address this, a complex stiffness matrix ($\sigma+i\omega$) can be constructed that takes into account the capacitive components of the electrode, tissue, or both. The result at each component frequency can be scaled and phase shifted, such as by using the results of the DFT. Fourth, the resulting waveform can be converted back to the time domain, such as by using an inverse Fourier transform provided by simulation software (e.g., Matlab). As an illustrative example, solutions can be calculated at 1024 frequencies between 0 and $1/(2*dt)$ Hz, where dt specifies the waveform time step size of $1\times10^{-5}$ s for voltage-controlled stimulation and $1\times10^{-6}$ s for current-controlled stimulation.

The capacitance value for a DBS can be approximated as 3.3 µF. The capacitance value for other neural tissue, like the spinal cord or a peripheral nerve, can also be approximated. In an example, the capacitance values of 3.3 µF, 1.65 µF, and 6.66 µF were tested, such as to characterize the sensitivity of the results on the value of this parameter. The electrode can be treated as purely capacitive with reversible (non-faradic) reactions occurring at the electrode-tissue interface. The tissue capacitance value for neural tissue can be estimated with upper and lower bounds for the dielectric constant K between $1\times10^4$ and $1\times10^6$ for frequencies below 1 kHz. The relationship between permittivity ($\in$) and dielectric constant is given by:

$$\in = K\in_0 \qquad (\text{Eq. 2})$$

where $\in_0$ is the permittivity of free space ($8.85\times10^{-12}$ $C^2/N\cdot m^2$). Therefore, permittivity values of $8.85\times10^{-8}$ F/m, $8.85\times10^{-7}$ F/m, and $8.85\times10^{-6}$ F/m can be employed with corresponding time constants ($\in/\sigma$) of $0.3\times10^{-6}$ s, $3\times10^{-6}$ s, and $30\times10^{-6}$ s.

Figure 8:
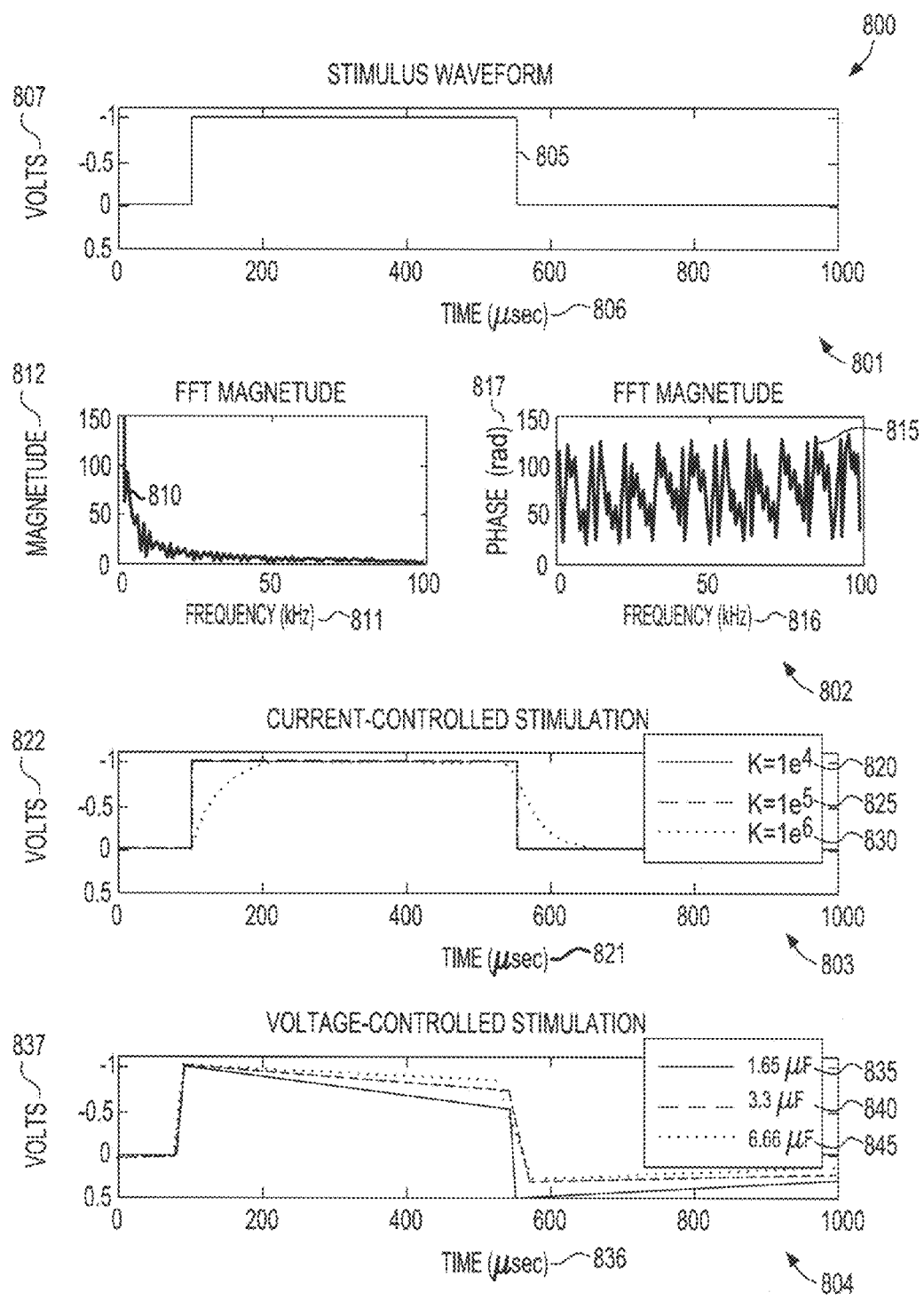
FIG. 8 illustrates generally an example of a method including performing the Fourier FEM method.

FIG. 8 illustrates generally an example of a method 800 including performing the Fourier FEM method. At 801, a stimulus waveform 805 is created in the time domain, shown with respect to time (µsec) 806 and volts 807.

At 802, the stimulus waveform 805 is converted to the frequency domain, such as by using a discrete Fourier transform. This results in an FFT magnitude 810, shown with respect to frequency (kHz) 811 and magnitude 812, and an FFT phase 815, shown with respect to frequency (kHz) 816 and phase (rad) 817.

At 803, a Fourier FEM solver is used to model a current-controlled stimulation. Estimated results for tissue capacitances having a dielectric constants K between $1\times10^4$ and $1\times10^6$ 820, 825, 830 are shown with respect to time (µsec) 821 and volts 822.

At 804, a Fourier FEM solver is used to model a voltage-controlled stimulation. Estimated results for DBS electrode capacitance values of 1.65 µF 835, 3.3 µF 840, and 6.66 µF 845 are shown with respect to time (µsec) 836 and volts 837.

ii. Neural Threshold Prediction

Figure 9:
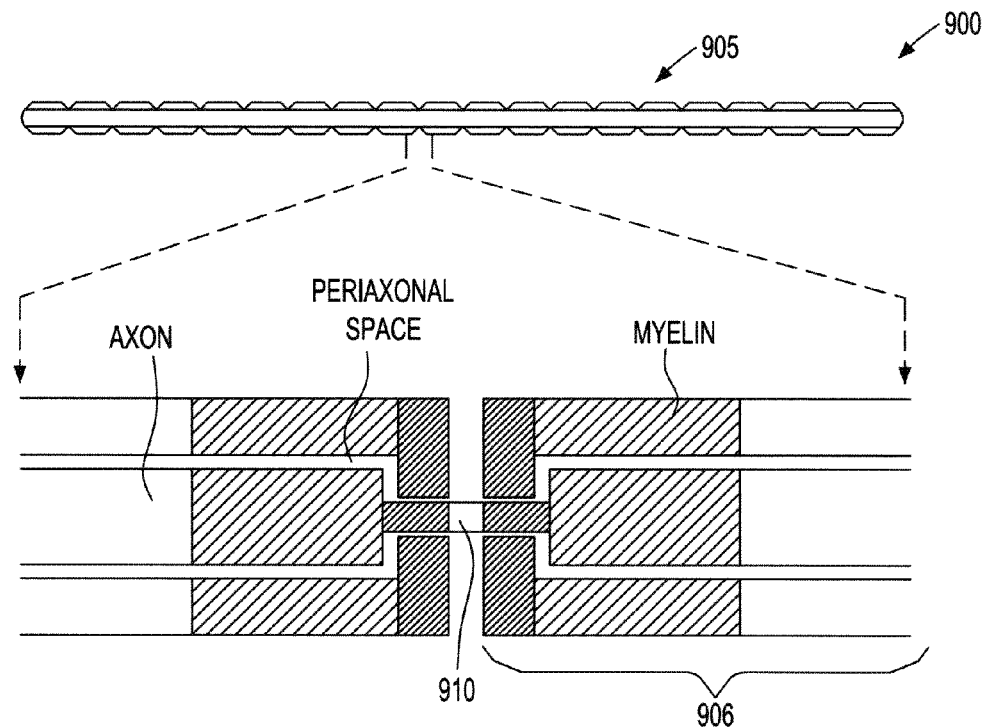
FIG. 9 illustrates generally an example of a model including a cable model axon for the calculation of stimulation thresholds.
Figure 9:
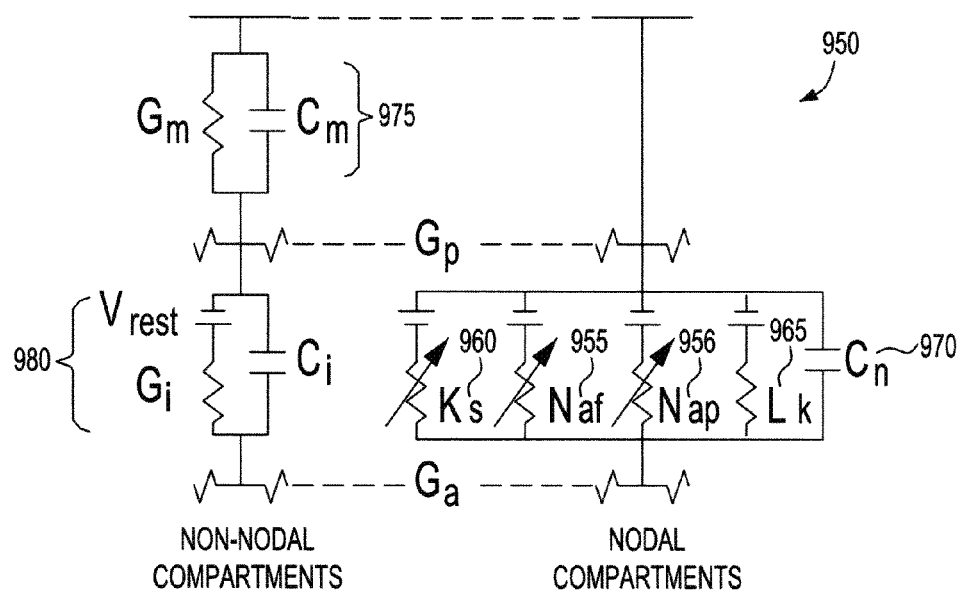

In an example, a field-axon simulation can be conducted using a Fourier FEM DBS electrode model coupled to 5.7 µm diameter myelinated axon models (see, e.g., FIG. 9). In this example, a collection of 119 model axons were distributed in a 17×7 matrix oriented perpendicular to the electrode shaft. In other examples, other numbers of model axons in other matrix orientations in other spatial orientations can be used. Specifically, for SCS, the fiber orientations, geometries, and densities will be different and are well-known. See e.g. FIGS. 7 and 8 in Feirabend et al., "Morphometry of human superficial dorsal and dorsolateral column fibres: significance to spinal cord stimulation," *Brain*, 125, 1137-1149 (2002), which is incorporated by reference herein. The perpendicular orientation of the axons to the electrode shaft can be used to identify the spatial extent of activation in the vertical and horizontal directions relative to the electrode shaft (localization of activation in axons oriented parallel to the shaft would be ambiguous in the vertical direction). In this example, the modeled axons were placed from 1 mm to 4 mm lateral to the modeled electrode, and from +4 mm above to −4 mm below the center of the modeled electrode contact (see, e.g., FIG. 10), though other distances can be used. The four model axons labeled with a "C" were used to evaluate strength-duration time constants (see FIG. 10). In this illustrative example, each model axon included 21 nodes of Ranvier with 0.5 mm internodal spacing. The voltage values from the Fourier FEM solution can be interpolated onto the length of the cable model, and the time-dependent transmembrane potential variations induced by the stimulation can be calculated using a neural simulator, (e.g., NEURON (www.neuron.yale.edu)). A range of square wave pulse widths from 60 μs to 450 μs were used in the simulations, corresponding to the range available from an implantable pulse generator (e.g., a Medtronic DBS pulse generator). At each axon and for each stimulus waveform, threshold stimulus amplitudes can be defined that generated action potentials in a one-to-one ratio with the stimulus frequency. The threshold values can be used to create two-dimensional contours to define the boundary of activation as a function of the stimulus amplitude. In this example, these two-dimensional boundary of activation contours can be swept around the axis of the electrode to determine the VTA.

FIG. 9 illustrates generally an example of a model 900 including a cable model axon 905 for calculating stimulation thresholds. In this example, the cable model axon 905 includes a 5.7 μm diameter myelinated cable model axon. In this example, each cable model axon 905 includes 21 nodes of Ranvier 910 having an internodal spacing of 0.5 mm. In this example, each internodal section 906 includes two paranodal myelin attachment segments (MYSA), two paranodal main segments (FLUT), and six internodal segments (STIN). The nodal membrane dynamics 950 can be modeled by a fast sodium ($N_{af}$) conductance 955 and persistent sodium ($N_{ap}$) conductance 956, slow potassium ($K_s$) conductance 960, and linear leakage ($L_k$)) conductance 965 in parallel with the nodal capacitance ($C_n$) 970. The STIN can be represented by a double cable structure of linear conductances with an explicit representation of the myelin sheath ($G_m$ in parallel with $C_m$) 975 and the internodal axolemma ($G_i$ in parallel with $C_i$) 980.

Figure 10:
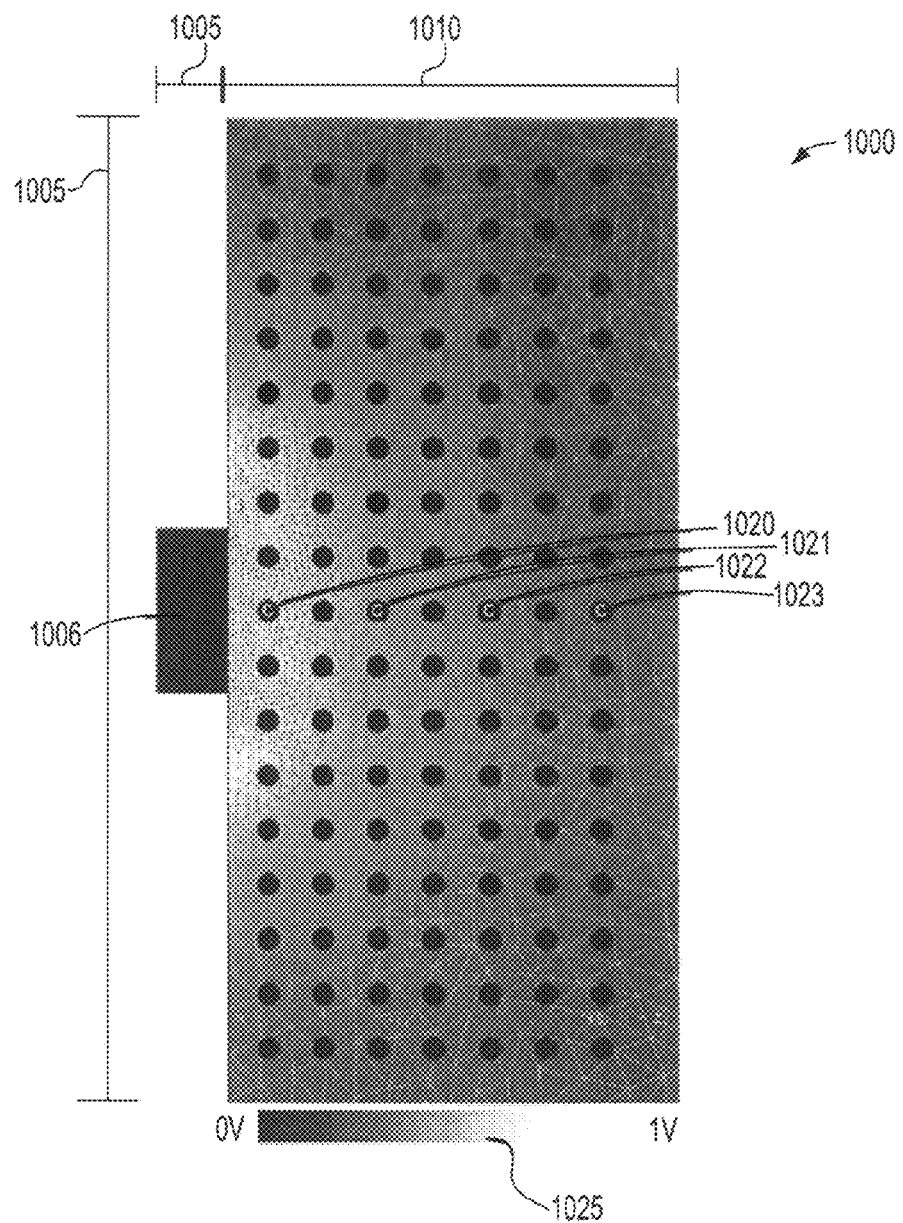
FIG. 10 illustrates generally an example of a model including an axisymmetric FEM model of an electrode and surrounding medium.

FIG. 10 illustrates generally an example of a model 1000 including an axisymmetric FEM model of an electrode 1005 and surrounding medium (mesh outline in background) 1010 (including cable model axons). In this example, the electrode 1005 is modeled as an electrical insulator having a contact 1006 as a voltage source or a current source. The surrounding medium (e.g., tissue medium) 1010 has a conductivity of 0.3 S/m and a dielectric constant from $1 \times 10^4$ F/m to $1 \times 10^6$ F/m. The capacitance of the electrode 1005 included a range from 1.66 μF to 6.65 μF. In this example, a 7×17 array of model axons (black circles, normal to the page) is oriented perpendicular to the electrode 1005 at distances from 1 mm to 4 mm lateral to the axis of the electrode 1005 in 0.5 mm increments, and from −4 mm to +4 mm vertically relative to the center of the electrode in 0.5 mm increments. Model axons 1020-1023 (labeled with a "C") are used for chronaxie calculation. Generally, the chronaxie is the minimum time over which an electric current twice the strength of the rheobase needs to be applied in order to stimulate a nerve cell, where the rheobase is typically the minimal electric current of infinite duration that results in an action potential of the nerve cell. The voltage solution 1025 within the surrounding medium 1010 (shown as background shading according to voltage solution 1025) can be interpolated onto the cable model axons to determine action potential threshold.

iii. Chronaxie Calculation

In an example, strength-duration curves can be generated for individual model axons using a range of pulse widths from 60 μs to 450 μs. In each case, the model axon can be oriented perpendicular to the shaft of the electrode 1005 at distances of 1 mm, 2 mm, 3 mm or 4 mm lateral from the axis of the electrode 1005 (see FIG. 10, model axons 1020-1023). In an example, the chronaxie estimates can be determined from the Weiss Equation modified for voltage-controlled stimulation:

$$V_{th}PW = V_{rh}PW + V_{rh}T_{ch} \quad \text{(Eq. 3)}$$

where $V_{th}$ is a threshold voltage, PW is a cathodic pulse width, $V_{rh}$ is a rheobase voltage, and $T_{ch}$ is a chronaxie. In this example, four conditions were assessed: (1) an electrostatic model with monophasic waveforms under monopolar stimulation; (2) a capacitive electrode model with monophasic waveforms under monopolar stimulation; (3) a capacitive electrode model with Medtronic waveforms under monopolar stimulation; and (4) a capacitive electrode model with Medtronic waveforms under bipolar stimulation. In this example, the Medtronic waveforms include waveforms based on direct measurements from a Medtronic Itrel II neurostimulator. In other examples, other experimental conditions can be tested. In this example, the modeled waveforms (e.g., Medtronic Itrel II modeled waveforms) were: (1) based on direct measurements from an actual stimulator; (2) biphasic; and (3) charge-balanced with a cathodic pulse equal to a user defined pulse width followed by an anodic recharge pulse. In this example, the anodic pulse began ~0.4 ms after the end of the cathodic pulse and ended ~4 ms before the beginning of the next cathodic pulse. Further, the pulse generator voltage was equal to the peak-to-peak voltage between the cathodic phase and the anodic phase of the stimulus waveform.

C. Exemplary Results

Generally, the effects of electrode capacitance and bulk tissue capacitance on the VTA can be quantified during voltage-controlled and current-controlled DBS or other forms of neuromodulation. Using the examples above, the effects of time-dependence of the electric field, stimulation waveform, and electrode configuration (monopolar or bipolar) on axonal stimulation thresholds can be addressed, as well as the influence of electrode capacitance on the strength-duration relationship generated under voltage-controlled DBS. Further, the results of these examples can be compared to clinical measurements.

i. Effects of Bulk Tissue Capacitance on the VTA

Bulk tissue capacitance can generally influence the time-course of the electric field generated in a tissue medium under the context of current-controlled stimulation. The difference in time course between the electrostatic model and the bulk tissue capacitance model can cause a difference in the VTA. This difference can be a function of the stimulation parameter settings. In an example, during current-controlled stimulation, larger errors can occur with shorter pulse widths due, at least in part, to the difference between the electrostatic and capacitive waveforms. Generally, the electrostatic and capacitive waveforms are greatest at the beginning of the cathodic phase. The difference between the capacitive and electrostatic models can be positively correlated with the dielectric value and stimulus amplitude, and can be diminished for longer pulse widths.

Figure 11:
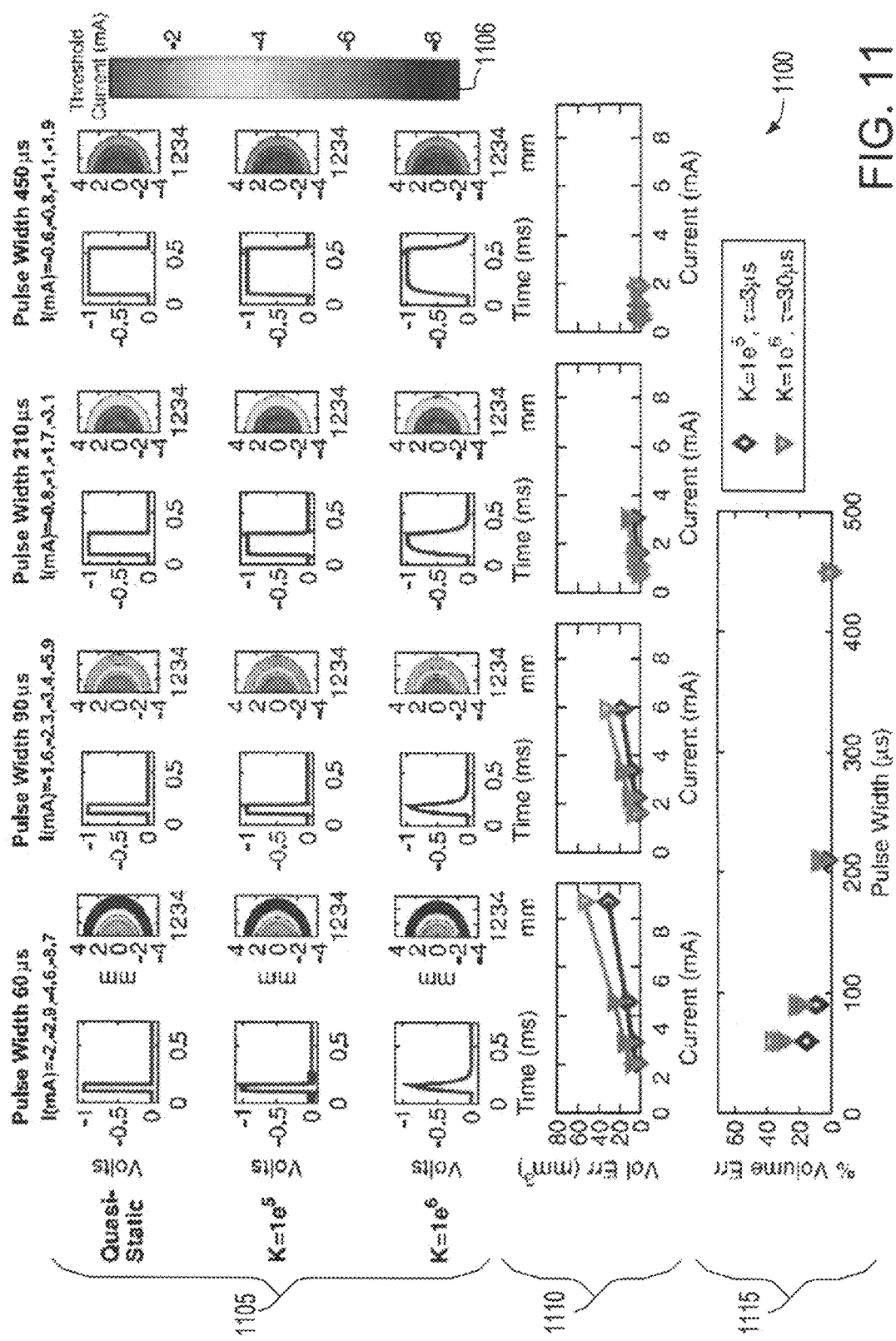
FIG. 11 illustrates generally examples of stimulation results including the VTA resulting from several current-controlled monopolar stimulations.

FIG. 11 illustrates generally examples of modeled stimulation results 1100 including the VTA resulting from several current-controlled monopolar stimulations. At 1105, pairs of graphs are shown organized by dielectric values (rows), including quasistatic, K=1e$^5$, and K=1e$^6$, and pulse widths (columns), including 60 µs, 90 µs, 210 µs, and 450 µs. The graphs on the left of each pair show time-dependent voltage waveforms as calculated by the Fourier FEM solver at one representative point in the volume. The graphs on the right of each pair are spatial filled contour plots of the extent of the VTA as determined by threshold amplitude values, which correspond to a scale 1106.

At 1110, graphs are shown that display the volume in cubic millimeters by which the electrostatic model overstates the VTA (Vol Err (mm$^3$)) compared to each dielectric value. Each graph is shown with respect to the stimulation current consistent with their respective column pulse width and current (I(ma)) from the time-dependent voltage waveforms at 1105. Further, the results are shown with respect to different dielectric values K=1e$^5$ and K=1e$^6$ having corresponding time constants τ=3 µs and τ=30 µs.

At 1115, the percent by which the electrostatic model overstates VTA (% Volume Err) for each pulse width and capacitance value across all current levels is shown as a function of pulse width for the current-controlled stimulations. The results are shown with respect to different dielectric values K=1e$^5$ and K=1e$^6$ having corresponding time constants τ=3 µs and τ=30 µs. In an example, the electrostatic model, for DBS stimulation parameter setting −3 mA, 90 µs, 130 Hz and K=1e$^6$, overestimates the VTA by ~18 mm$^3$, or ~20%. This effect can be modulated by the dielectric constant of the tissue medium and the impedance of the volume (e.g., the impedance of this model is ~400Ω). Larger dielectric values can cause the system to have a longer time constant (τ=RC), which can exacerbate the magnitude of the electrostatic error.

ii. Effects of Electrode Capacitance on the VTA

Electrode capacitance can generally influence the time-course and amplitude of a stimulus waveform transmitted to a tissue medium under the context of voltage-controlled stimulation. The differences between the stimulus waveforms of the electrostatic and electrode capacitance models can result in different VTAs as a function of the stimulation parameters. In an example, during voltage-controlled stimulation, the difference between the capacitive and electrostatic models can be inversely proportional to the capacitance value, and can be greater for longer pulse widths and larger stimulus amplitudes.

Figure 12:
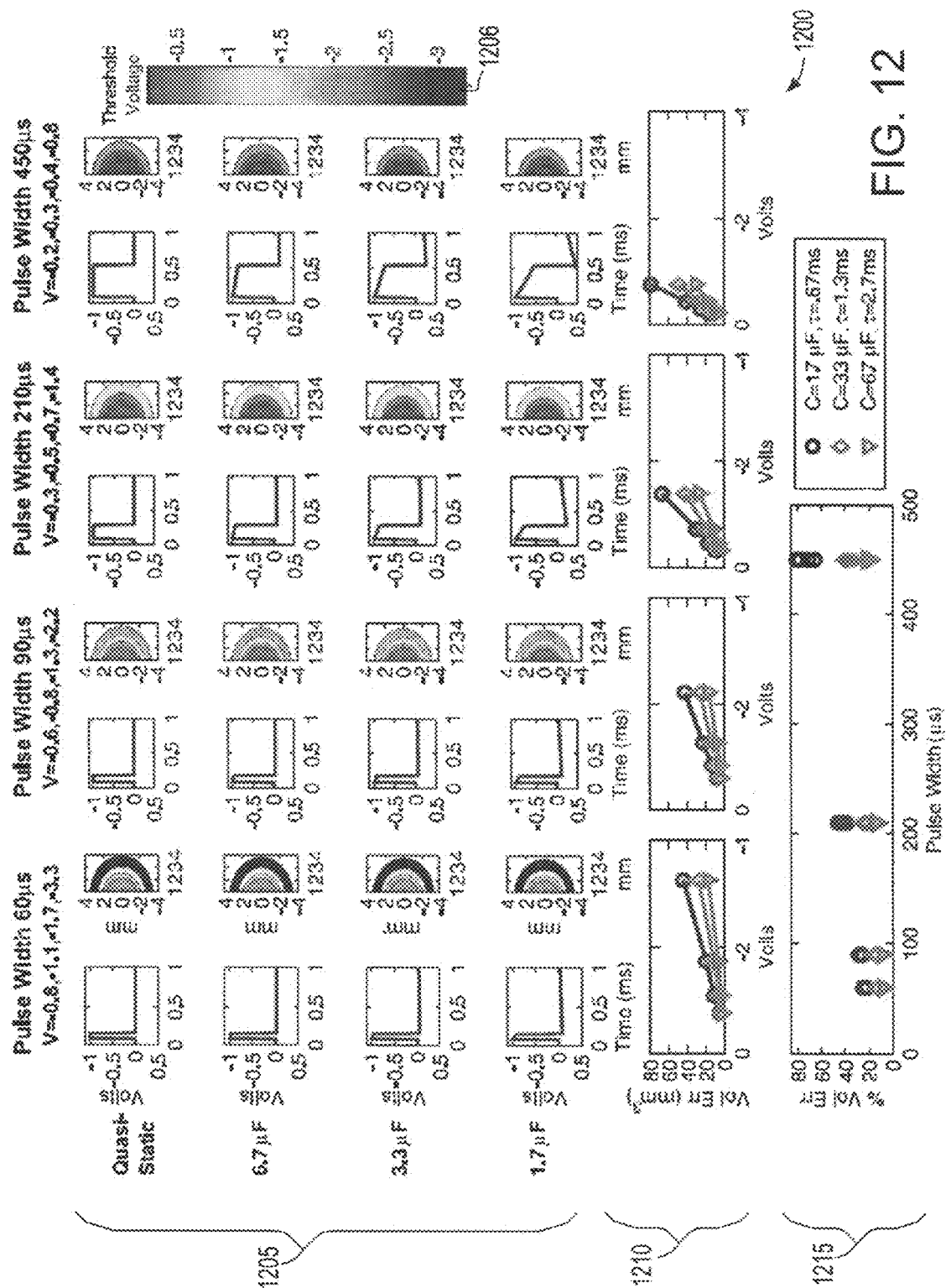
FIG. 12 illustrates generally examples of stimulation results including the VTA resulting from several voltage-controlled monopolar stimulations.

FIG. 12 illustrates generally examples of stimulation results 1200 including the VTA resulting from several voltage-controlled monopolar stimulations. At 1205, pairs of graphs are shown organized by capacitance values (rows), including quasistatic, 6.7 µF, 3.3 µF, and 1.7 µF, and pulse widths (columns), including 60 µs, 90 µs, 210 µs, and 450 µs. The graphs on the left of each pair show time-dependent voltage waveforms as calculated by the Fourier FEM solver at one representative point in the volume. The graphs on the right are spatial filled contour plots of the extent of the VTA as determined by threshold amplitude values, which correspond to a scale 1106.

At 1210, graphs are shown that display the volume in cubic millimeters by which the electrostatic model overstates the VTA (Vol Err (mm$^3$)) compared to each capacitance value. Each graph is shown with respect to the stimulation voltage consistent with their respective column pulse width and voltage (V) from the time-dependent voltage waveforms at 1205. Further, the results are shown with respect to different capacitance values C=1.7 µF, C=3.3 µF, and C=6.7 µF having corresponding time constants τ=0.67 ms, τ=1.3 ms and τ=2.7 ms.

Figure 13:
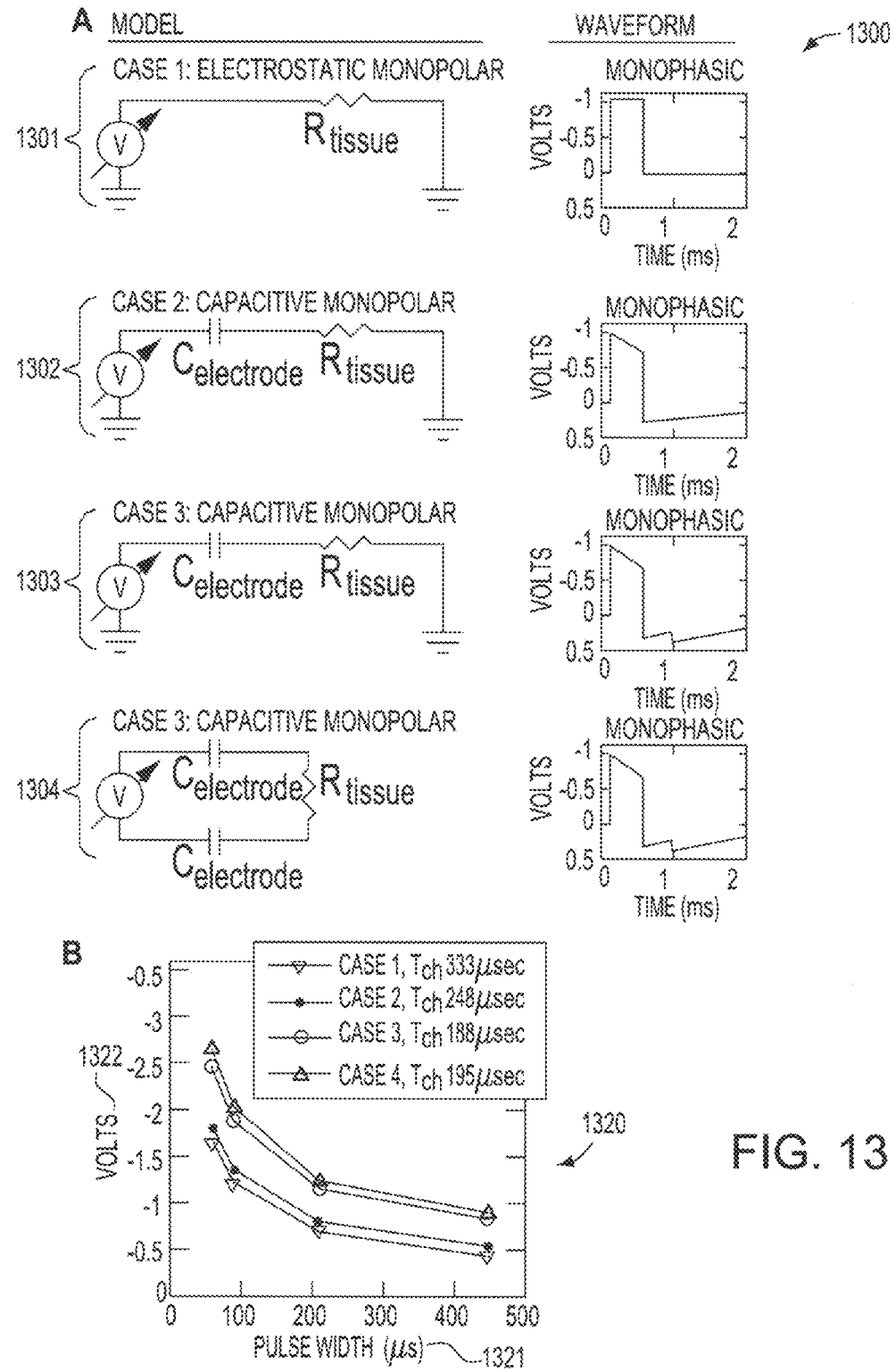
FIG. 13 illustrates generally examples of methods including calculating threshold stimulation values, as a function of pulse width, for axons oriented perpendicular to an electrode shaft.

At 1215, the percent by which the electrostatic model overstates VTA (% Volume Err) for each pulse width and capacitance value across all current levels is shown as a function of pulse width for the voltage-controlled stimulations. The results are shown with respect to different capacitance values C=1.7 µF, C=3.3 µF, and C=6.7 µF having corresponding time constants τ=0.67 ms, τ=1.3 ms and τ=2.7 ms. In an example, the electrostatic model, for DBS stimulation parameter setting −3 mA, 90 µs, 130 Hz and a standard electrode capacitance value of C=3.3 µF, overestimates the VTA by ~30 mm$^3$, or ~20%. This effect can be modulated by the dielectric constant of the tissue medium and the impedance of the volume (e.g., the impedance of this model is ~400Ω). Smaller capacitance values cause the system to have a shorter time constant (τ=RC), which can exacerbate the magnitude of the electrostatic error.

iii. Effects of Electrode Capacitance and Stimulation Waveform on the Strength-Duration Relationship FIG. 13 illustrates generally examples of methods 1300 including calculating threshold stimulation values, as a function of pulse width, for axons oriented perpendicular to an electrode shaft. The method 1300 includes calculating under four conditions: Case 1: Electrostatic Monopolar 1301, an electrostatic model with monophasic waveforms under monopolar stimulation; Case 2: Capacitive Monopolar 1302, a capacitive electrode model with monophasic waveforms under monopolar stimulation; Case 3: Capacitive Monopolar 1303, a capacitive electrode model with Medtronic waveforms under monopolar stimulation; and Case 4: Capacitive Bipolar 1304, a capacitive electrode model with Medtronic waveforms under bipolar stimulation.

In this example, a 3 mm electrode-to-axon distance resulted in calculated threshold voltages comparable to those recorded in clinical DBS strength-duration experiments. However, it should be noted that in this example, the impedance of the model (~400Ω) is lower than the commonly observed clinical measurement (~1000Ω). In turn, the VTA for a given stimulus voltage in this example is an overestimation of the VTA generated with higher impedance electrodes.

In the example of FIG. 13, graph 1320 shows strength-duration curves for the four cases 1301-1304 with respect to pulse width (µs) 1321 and volts 1322. During this example, independent of the impedance of the model, the threshold amplitudes progressively increased and $T_{ch}$ progressively decreased from Case 1 1301 through Case 3 1303 for an axon stimulated at 130 Hz, while Case 3 1303 and Case 4 1304 had substantially similar results (see graph 1320). These results show that incremental changes in the model realism can generate measurable changes in model output. In addition, typical experimental estimates of $T_{ch}$ (~100 µs) from DBS subjects match most closely with our more realistic DBS models.

Chronaxie values were also dependent on electrode-to-axon distance, stimulus waveform, and stimulation frequency. In an example, the $T_{ch}$ of axons 1 mm, 2 mm, 3 mm, and 4 mm lateral from an electrode axis were 238 µs, 296 µs, 333 µs and 356 µs respectively for 130 Hz stimulation under the conditions of Case 2 1302. In other examples, the chronaxie values between Case 2 1302, Case 3 1303, and Case 4 1304 were also compared at 100 Hz (generally the lowest recommended frequency for typical clinical DBS for movement disorders), 130 Hz (a common frequency for clinical DBS) and 185 Hz (the maximum frequency for the Medtronic pulse generator). The results of these examples are summarized in Table 1 for axons located 3 mm from the electrode axis and generally show that $T_{ch}$ is dependent on both stimulus waveform and frequency. The Medtronic waveform generated a decreasing $T_{ch}$ with increasing stimulation frequency, while the monophasic waveform exhibited a slight increase in $T_{ch}$ over the same frequency range.

TABLE 1

DBS chronaxie values

| Waveform | Configuration | $T_{ch}$ (µs), 100 Hz | $T_{ch}$ (µs), 130 Hz | $T_{ch}$ (µs), 185 Hz |
|---|---|---|---|---|
| Monophasic | Monopolar | 235 | 246 | 262 |
| Medtronic | Monopolar | 204 | 188 | 144 |
| Medtronic | Bipolar | 214 | 195 | 126 |

D. Discussion of Exemplary Results

Explicit representation of electrode capacitance is helpful for accurate estimation of the VTA generated by voltage-controlled stimulation. Explicit representation of the bulk tissue capacitance can be helpful for accurate estimation of the VTA generated by current-controlled stimulation, depending on the dielectric constant of the tissue medium. Further, DBS strength-duration time constants are dependent on capacitive components of the electrode-tissue interface and the actual Medtronic stimulation waveform (versus a monophasic waveform). Although the examples above were concentrated on DBS technology, they are applicable to the field of neurostimulation in general such as spinal cord stimulation and stimulation of the peripheral nervous system including cranial nerves as outlined above.

i. Electrical Model of the Electrode-Tissue Interface

In an example, electrical circuit models of the electrode-tissue interface typically include a double-layer capacitance ($C_{dl}$) of the electrode in parallel with a lumped non-linear complex impedance ($Z_{Faradic}$). $Z_{Faradic}$ typically becomes activated when the stimulation exceeds the charge carrying capacity of the $C_{dl}$. In this example, the electrode was modeled as a pure capacitor. In this example, the source, electrode and tissue medium was modeled with a set of circuit diagrams (see e.g., FIG. 14). In this example, the electrode contact is perfectly polarizable, and only non-faradaic (reversible) reactions are occurring at the electrode-tissue interface. The charge storage capacity of platinum-iridium electrodes (as used in DBS) is ~100 µC/cm², sufficiently exceeding a 30 µC/cm² limit typically employed in clinical neurostimulation. The neural tissue medium can be crudely represented with bulk capacitance and conductivity values.

The parameters of this example generally limit the effects of the capacitive components to specific stimulation types. In an example, the tissue capacitance will only exert an influence during constant current stimulation because the electrode and tissue components behave as independent circuits. Independent of the stimulus waveform, all of the stimulus current will pass through the tissue, and as such, the electrode capacitance can be ignored. In an example, using monophasic waveforms does not allow the capacitance to discharge, resulting in voltage increases during each pulse. In another example, using charge-balanced, biphasic waveforms serves to discharge the capacitance during each waveform cycle. In other examples, the effects of the tissue capacitance can be ignored during voltage-controlled stimulation because capacitance of the DBS electrode can be of a value two orders of magnitude greater than the tissue capacitance. As a result, during voltage-controlled stimulation the voltage change across the neural tissue capacitance is much smaller than across the electrode capacitance.

Tissue capacitance values are generally a property of a neural medium, and as such, the tissue capacitance values are unlikely to change substantially in different experimental conditions. Electrode capacitance, on the other hand, is generally a function of the electrode material and size. In certain examples, electrodes with limited charge carrying capacity or small size can reduce the electrode capacitance to a point where interaction between both tissue and electrode capacitances may affect the stimulus waveform transmitted to the tissue. Greater VTA errors typically result from smaller capacitance values and smaller electrode time constants. In an example, both of the electrode and tissue capacitances can be discharged at the onset of a stimulation pulse. In this example, the voltage changes at the rate dV/dt (the tissue resistance is momentarily ignored). The equivalent capacitance of the system for two capacitors in series is given by:

$$C_{eq}=(C1 \times C2)/(C1+C2) \qquad \text{(Eq. 4)}$$

and the current is given by:

$$i(t)=C_{eq}dV/dt \qquad \text{(Eq. 5)}$$

Thus, in this example, the total current is limited by the rise time of the voltage, which is infinite in theory but finite-valued in model experiments (due to nonzero dt values) and in actual DBS pulse generators. The voltage across each capacitor can now be calculated from:

$$V(t)\frac{1}{C}\int i(t)dt \qquad \text{(Eq. 6)}$$

This equation demonstrates that the voltage across each capacitor at the end of the stimulus onset is inversely proportional to its capacitance value. Therefore, in this example, the electrode and tissue capacitors act as an effective voltage divider, generally reducing the maximum amplitude of the stimulus applied to the tissue. In certain examples, this can further exacerbate the differences between the electrostatic and Fourier FEM models. In examples using DBS electrodes, this effect can cause a difference of ~1% in the amplitude of the tissue voltage waveform. In an example using an electrode $\frac{1}{10}^{th}$ the size of the DBS electrode, this effect can cause a 10% amplitude reduction in the tissue voltage waveform. Further, in an example using an electrode $\frac{1}{100}^{th}$ the size of the DBS electrode, this effect can cause a 50% amplitude reduction in the tissue voltage waveform.

Figure 14:
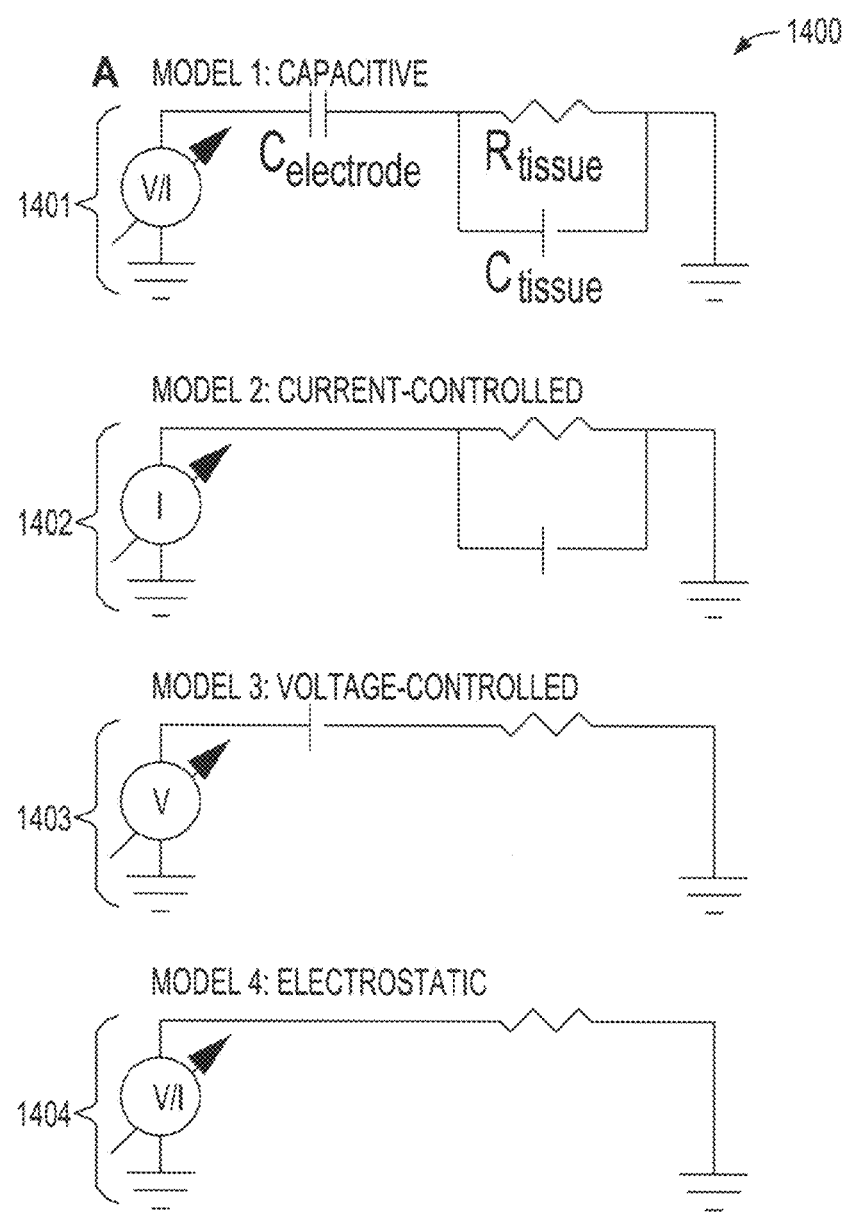
FIG. 14 illustrates generally examples of circuit diagrams including equivalent circuit diagrams of neural stimulation field models, including: Model 1: Capacitive; Model 2: Current-Controlled; Model 3: Voltage-Controlled; and Model 4: Electrostatic.

FIG. 14 illustrates generally examples of circuit diagrams 1400 including equivalent circuit diagrams of neural stimulation field models, including: Model 1: Capacitive 1401; Model 2: Current-Controlled 1402; Model 3: Voltage-Controlled 1403; and Model 4: Electrostatic 1404. Model 1 1401 illustrates generally a neural stimulation system including a voltage or a current source, an electrode capacitance ($C_{electrode}$), a tissue resistance ($R_{tissue}$), and a tissue capacitance ($C_{tissue}$). Model 2 1402 illustrates generally a current-controlled neural stimulation system where the electrode capacitance can be ignored. Model 3 1403 illustrates generally a voltage-controlled neural stimulation system with a DBS electrode, where the tissue capacitance can be ignored. Model 4 1404 illustrates generally an electrostatic approximation neural stimulation system which includes only tissue resistance.

Figure 15:
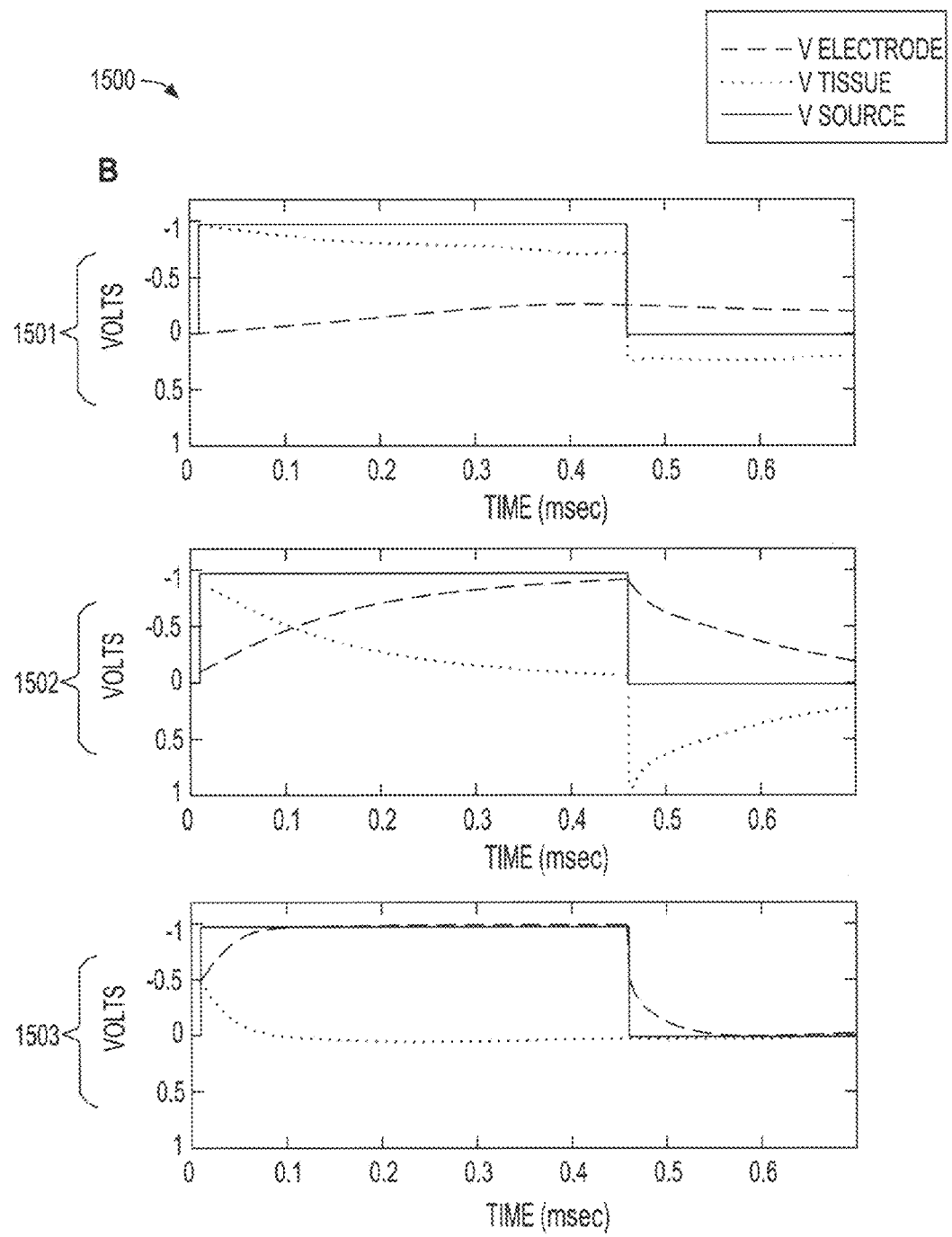
FIG. 15 illustrates generally an example of resulting waveforms including three cases illustrating the interaction between electrode and tissue capacitance that can occur during voltage-controlled stimulation when the values of the electrode and tissue capacitances are comparable.

FIG. 15 illustrates generally an example of resulting waveforms 1500 including three cases illustrating the interaction between electrode and tissue capacitance that can occur during voltage-controlled stimulation when the values of the electrode and tissue capacitances are comparable. The resulting waveforms 1500 illustrate three cases: Case 1 (DBS electrode) 1501; Case 2 (having a $C_{electrode}/C_{ratio}$ of 10) 1502; and Case 3 (having a $C_{electrode}/C_{tissue}$ ratio of 1) 1503. Case 1 1501 illustrates that the interaction between a DBS electrode and tissue capacitance can cause an error of about 1% in $V_{tissue}$, and τ=1.3 ms. Case 2 1502 illustrates that the interaction between electrode and tissue capacitance having a ratio of $C_{electrode}/C_{tissue}$≈10 can cause an error of about 10% in $V_{tissue}$, and τ=163 μs. Case 3 1503 illustrates that the interaction between electrode and tissue capacitance having a ratio of $C_{electrode}/C_{tissue}$≈1 can cause an error of about 50% in $V_{tissue}$ and τ=28.7 μs.

ii. Implications for Modeling of Clinical Neurostimulation

Generally, detailed computer modeling techniques can provide insight into the fundamental mechanisms of electrical stimulation of the nervous system including the central nervous system and the peripheral nervous system. In addition, limitations in the understanding of the therapeutic mechanisms of DBS make it interesting to use neurostimulation modeling to estimate the VTA during therapeutic and non-therapeutic stimulation. In an example, this information can be used to develop correlations between activation of anatomical nuclei and other sites and either therapeutic outcomes or side effects of the stimulation.

Clinical neurostimulation pulse generators can use either voltage-controlled or current-controlled stimulation. In either of these cases, the capacitance can modulate the time dependent properties of the stimulus waveform transmitted to the tissue medium. Failure to represent these reactive components in neurostimulation models can in certain circumstances cause significant errors in VTA calculations. In certain examples, this can be particularly relevant during DBS, where an error of ~30 mm³ (overestimation with quasistatic assumption and typical therapeutic stimulation parameters) could account for ~15% of a target volume such as the subthalamic nucleus.

In certain examples, qualitative comparisons can be made between our results and clinical records, and such useful comparisons may only become evident with a model that explicitly accounts for the actual stimulus waveform and electrode capacitance effect, such as for voltage-controlled stimulation. In certain examples, the calculation of $T_{ch}$ for axonal stimulation best matches clinical results with the more detailed model that accounts for stimulus waveform and electrode capacitance. In addition, including the specific Medtronic waveform in the model caused decreasing neuronal activation thresholds and decreasing $T_{ch}$ with increasing stimulus frequency. These examples highlight the value of incorporating details that have previously been ignored in neurostimulation modeling, such as capacitance of the electrode-tissue interface and actual stimulus waveforms generated by clinical devices.

The use of the quasistatic (electrostatic) assumption can cause significant errors in estimating neural activation during current-controlled or voltage-controlled stimulation. The differential effects between voltage-controlled and current-controlled stimulation can be caused by electrode capacitance and tissue capacitance, respectively. The errors typically induced by ignoring the capacitance of the electrode-tissue interface can be a function of the stimulus waveform, stimulus amplitude, and the magnitude of the reactive components. Thus, the development of realistic estimates of the VTA from clinical neurostimulation devices should incorporate bioelectric field models that account for one or both of the electrode or bulk tissue capacitance.

3. Sources and Effects of Electrode Impedance During Deep Brain Stimulation

A. Introduction

DBS and other forms of neuromodulation can excite axons surrounding the electrode. While correlations between axonal activation and the therapeutic mechanisms of DBS and other forms of neuromodulation remain unclear, it is believed that high frequency stimulation overrides underlying pathological neural activity patterns. However, a wide range of factors can influence the clinical response to DBS and other forms of neuromodulation, including the disease state of the subject, the anatomical target selected for stimulation, the location of the electrode within the target, the electrode geometry, and the selection of stimulation parameters (e.g., voltage, pulse width, and frequency). In clinical DBS devices using voltage-controlled stimulation, the amount of current delivered to the tissue can depend on the electrode impedance. Clinical measurements of DBS electrode impedance typically range from 500Ω to 1500Ω. SCS electrode impedance generally ranges from 200-750 Ohms. However, the factors that influence this variability, or how this range of electrode impedance affects the spatial extent of neural stimulation, are unclear.

Several factors can contribute to DBS electrode impedance values, including: the connections between an implanted pulse generator (IPG) and an electrode; the surface area of the electrode or the IPG; the conductivity or thickness of an encapsulation layers that surround the electrode or the IPG; and the conductivity of the bulk tissue medium. FDA approved DBS devices include the quadripolar Medtronic 3387-89 DBS electrode and IPG system. The Medtronic Itrel II and Soletra IPGs can record impedances of up to 2,000Ω, while the Medtronic Kinetra measures up to 4,000Ω. High impedance values are often associated with lead breakage or some other mechanical failure, especially if the current is less than 15 μA. Alternately, very low impedance values (<50Ω) with high current levels (>250 mA) can be associated with a short circuit in the hardware. Between these extremes, little clinical attention is typically paid to the impedance when selecting therapeutic stimulation parameter settings for individual subjects. However, the large range of impedances suggests that current delivery and the subsequent neural response to DBS could be substantially different from subject-to-subject and from contact-to-contact.

In an example, the sensitivity of electrode impedance (e.g., from the range of 500Ω to 1500Ω typically observed with clinical DBS) can be observed, such as to detect changes in the properties of electrode(s) and tissue medium, and determine how the variable electrode impedance affects the VTA.

B. Exemplary Methods

In an example, the origin and impact of electrode impedance in DBS and other forms of neuromodulation can be addressed, such as by primarily focusing on the electrode-tissue interface. A range of detailed computer models can be developed with various geometrical and electrical properties to characterize likely sources of impedance variability in clinical DBS and other neuromodulation devices. Models of neurostimulation that integrate finite-element based electric field solutions and multi-compartment cable models of myelinated axons can be used to predict the VTA generated by DBS and other forms of neuromodulation under different impedance conditions.

i. Deep Brain Stimulation Finite Element Model

Figure 16:
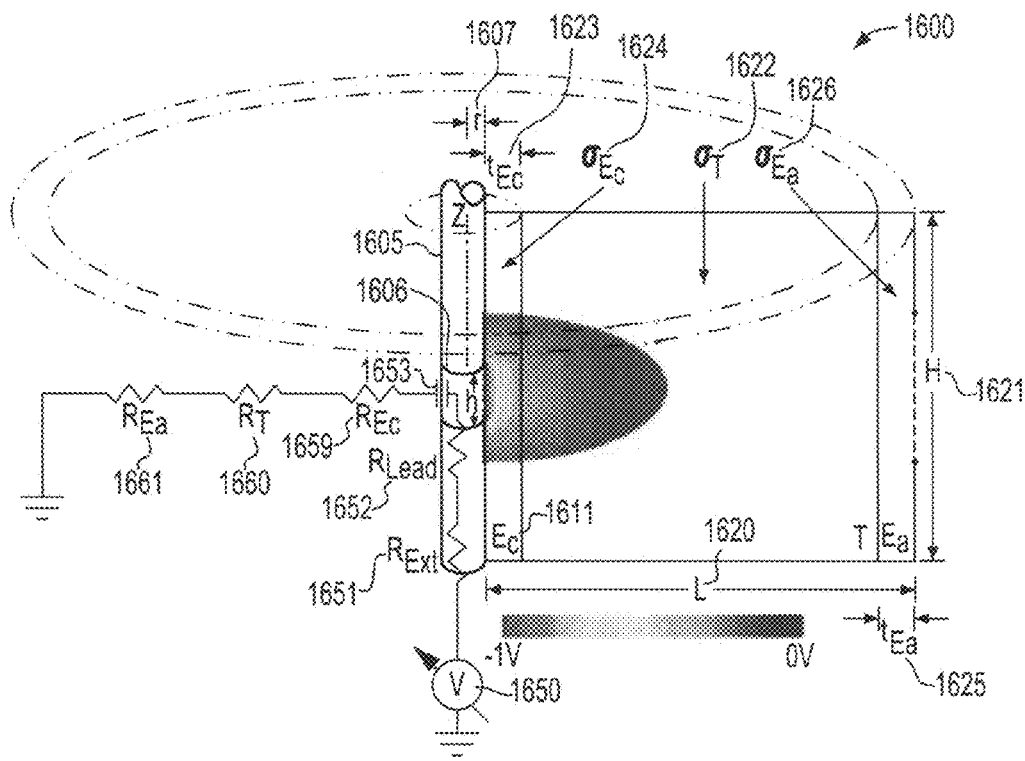
FIG. 16 illustrates generally an example of a system including an axisymmetric finite element model (FEM) with ~80,000 nodes created using multiphysics modeling software to represent a DBS electrode and surrounding tissue medium, including an electrode encapsulation layer (Ec), a bulk tissue medium (T), and an IPG encapsulation layer (Ea).

FIG. 16 illustrates generally an example of a system 1600 including an axisymmetric finite element model (FEM) with ~80,000 nodes created using multiphysics modeling software (e.g., FEMLAB 3.1) to represent a DBS electrode 1605 and surrounding tissue medium 1610, including an electrode encapsulation layer (Ec) 1611, a bulk tissue medium (T) 1612, and an IPG encapsulation layer (Ea) 1613. In this modeled example, the DBS electrode 1605 and a single electrode contact 1606 were centered on the z axis, surrounded by the tissue medium 1610. In an example, an indifferent electrode can be placed on the outer boundary of the axisymmetric model and designed to match the surface area of an IPG (e.g., ~56.5 cm$^2$).

Several models were created to explore the effects of different geometrical properties and conductivities on DBS impedance. The model can include a cathode (the DBS electrode contact) and an anode (the indifferent or return electrode of the IPG case) to mimic the monopolar stimulation condition commonly used in clinical practice. Variable density FEM meshes can be used to increase solution accuracy by providing a mesh density that is highest where the electric field gradient is largest. The voltage within the volume can be determined using a Fourier FEM solver that solves the Poisson equation in time and space concurrently. In an example, the solver can be used to combine the actual DBS waveform and the capacitance of the electrode-tissue interface into the bioelectric field model. In this example, the Poisson equation can solved using direct matrix inversion (UMFPACK solver), such as at 512 frequencies between 0 Hz (DC) and 5000 Hz to determine the potential distribution (Ve) generated within the tissue medium (stiffness matrix σ) based on a collection of sources (I):

$$\nabla \cdot \sigma \nabla V_e = -I \quad \text{(Eq. 7)}$$

The Fourier FEM solver can use the solution of the Poisson equation at each component frequency, along with the fast Fourier transform (FFT) of the stimulation waveform, to determine the time dependent waveform at various locations in the axisymmetric volume.

i. Impedance Model

As an illustrative example, the sensitivity of electrode impedance to several model parameters can be observed by manipulating a model (having an impedance of 1003Ω) specified in Table 2 and FIG. 16. The model can be used to analyze the sensitivity of impedance to changes in dimensions of the volume conductor. Variations in length (L) 1620 from 50-300 mm and height (H) 1621 from 20-120 mm are intended to reflect the path of allowable current flow between the IPG and the electrode contact 1606. In certain examples, the length (L) 1620 can be representative of the distance from the DBS electrode contact to the IPG, while the height (h) 1621 can be representative of the diameter of the head and neck. In certain examples, tissue conductivity ($\sigma_T$) 1622 was varied from 0.15-0.3 S/m.

In other examples, the model can additionally or alternatively be used to analyze the effects of changes in electrode contact size. The dimensions of the electrode (e.g., the cylindrical Medtronic 3387-89 DBS electrode) contacts can be specified as 1.5 mm height by 1.27 mm diameter, as an example. However, these values can vary up to 0.1 mm in height or diameter, such as due to manufacturing tolerances. Further, the model can also be used to analyze the effects of varied thickness and conductivity of the encapsulation layer around the electrode contact ($t_{Ec}$ 1623 and $\sigma_{Ec}$ 1624 respectively) and around the IPG ($t_{Ea}$ 1625 and $\sigma_{Ea}$ 1626 respectively). In this example, modeled encapsulation thickness ($t_{Ec}$) 1623 ranged from 0.1-1.0 mm, and modeled encapsulation conductivity ($\sigma_{Ec}$) 1624 ranged from 0.05-0.15 S/m.

TABLE 2

Impedance model

| Parameter | Nominal value | Range |
|---|---|---|
| Volume conductor height (H) 1621 | 40 mm | 20-120 mm |
| Volume conductor length (L) 1620 | 120 mm | 50-300 mm |
| Electrode encapsulation thickness ($t_{Ec}$) 1623 | 0.5 mm | 0.1-1.0 mm |
| IPG Encapsulation thickness ($t_{Ea}$) 1625 | 0.5 mm | 0.0-1.0 mm |
| Electrode contact height (h) 1606 | 1.5 mm | 1.4-1.6 mm |
| Electrode contact radius (r) 1607 | 0.635 mm | 0.585-0.685 mm |
| Contact encapsulation conductivity ($\sigma_{Ec}$) 1624 | 0.1 S/m | 0.05-0.2 S/m |
| Tissue conductivity ($\sigma_T$) 1622 | 0.2 S/m | 0.15-0.3 S/m |
| IPG encapsulation conductivity ($\sigma_{Ea}$) 1626 | 0.1 S/m | 0.05-0.15 S/m |

The example of FIG. 16 shows an equivalent circuit diagram of the DBS system. For each model, a −1 V DC stimulus can be applied using a source 1650 located between the cathodal contact and the IPG, and the voltage distribution within the volume can be determined. Current density can be integrated around the contact surface, such as to determine the current injected into the volume. Ohms law can be used to determine the impedance from Z=V/I. The equivalent circuit of FIG. 16 can include a wire resistance ($R_{ext}$ 1651 and $R_{Lead}$ 1652, e.g., 40Ω and 40Ω respectively) and a capacitance of the electrode contact (C 1653) to enable a more accurate comparison with clinical DBS impedance measurements. This example also models an electrode encapsulation layer impedance ($R_{ec}$) 1659, a bulk tissue impedance ($R_T$) 1660, and an IPG encapsulation layer impedance ($R_{Ea}$) 1661. In this example, the model impedances can be calculated at the onset of the cathodic phase of the stimulation pulse, and can therefore be independent of voltage or pulse width.

iii. Estimation of the Volume of Tissue Activated

In an example, field-axon simulations were conducted using Fourier FEM DBS electrode models coupled to 5.7 μm diameter myelinated axon models. In this example, a collection of 119 model axons were distributed in a 17×7 matrix, which can be oriented perpendicular to the electrode shaft. This orientation of axons can be used to identify the spatial extent of activation in the vertical and horizontal directions relative to the electrode shaft (localization of activation in axons oriented parallel to the shaft would be ambiguous in the vertical direction). In this example, the modeled axons were placed from 1 mm to 4 mm lateral to the modeled electrode and from +4 mm above to −4 mm below the center of the modeled electrode contact. In this example, each axon included 21 nodes of Ranvier with 0.5 mm internodal spacing.

The stimulus waveforms can be based on modeled waveforms (e.g., Medtronic Itrel II modeled waveforms). Such waveforms can be biphasic and charge-balanced with a cathodic pulse equal to the user-defined pulse width followed by an anodic recharge pulse. The anodic pulse began 0.4 ms after the end of the cathodic pulse and ended 4 ms before the beginning of the next cathodic pulse. The IPG output voltage can be equal to the peak-to-peak voltage between cathodic and anodic phases of the stimulus waveform. The time-dependent potential distribution generated in the tissue medium from the Fourier FEM solution can be interpolated onto the length of each cable model, and the time-dependent transmembrane potential variations induced by the stimulation can be calculated in a neural simulator (e.g., NEURON v5.7). Threshold stimulus amplitudes can be defined to generate action potentials in a one-to-one ratio with the stimulus frequency. The threshold stimulus values can be used to create 2D contours to define a boundary of activation as a function of the stimulus amplitude. These 2D boundary of activation contours can be swept around the axis of the electrode to determine the VTA volume. Three-dimensional renderings and VTA calculations relative to the thalamus can be performed using a bioelectric field solver (e.g., BioPSE).

C. Exemplary Results

Factors that influence DBS electrode impedance can be identified and the effects of the DBS electrode impedance variability on the VTA during voltage-controlled DBS or other forms of neuromodulation can be quantified.

i. Effects of the Volume Conductor Geometry on Impedance

Figure 17:
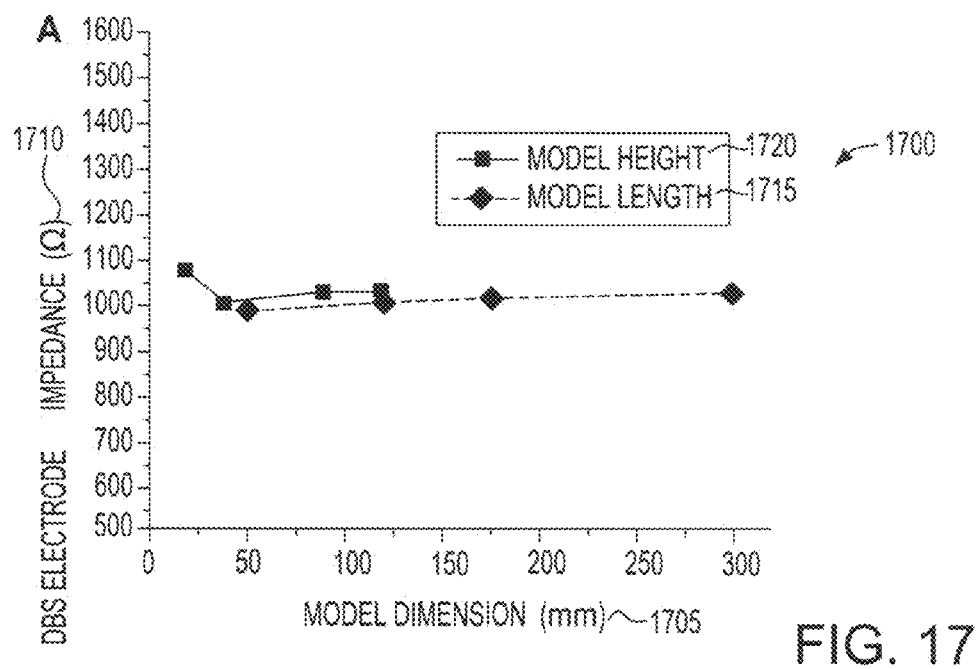
FIG. 17 illustrates generally an example of a relationship illustrating, generally, variations in dimensions of the overall volume conductor model and the resulting effect on impedance values.

FIG. 17 illustrates generally an example of a relationship 1700 illustrating, generally, variations in dimensions of the overall volume conductor model and the resulting effect on the DBS electrode impedance values. Generally, variations in dimensions of the overall volume conductor model had a weak effect on DBS electrode impedance values. Increases in model length 1715 (e.g., volume conductor length (L) 1620) over the range 50-300 mm caused an increase in the DBS electrode impedance ($\Omega$) 1710 of $\Delta Z \approx 38\Omega$, and increases in model height 1720 (e.g., volume conductor height (H) 1621) from 20-120 mm caused a decrease in the DBS electrode impedance ($\Omega$) 1710 of $\Delta Z \approx 48\Omega$.

ii. Effects of Electrode Dimensions on Impedance

Figure 18:
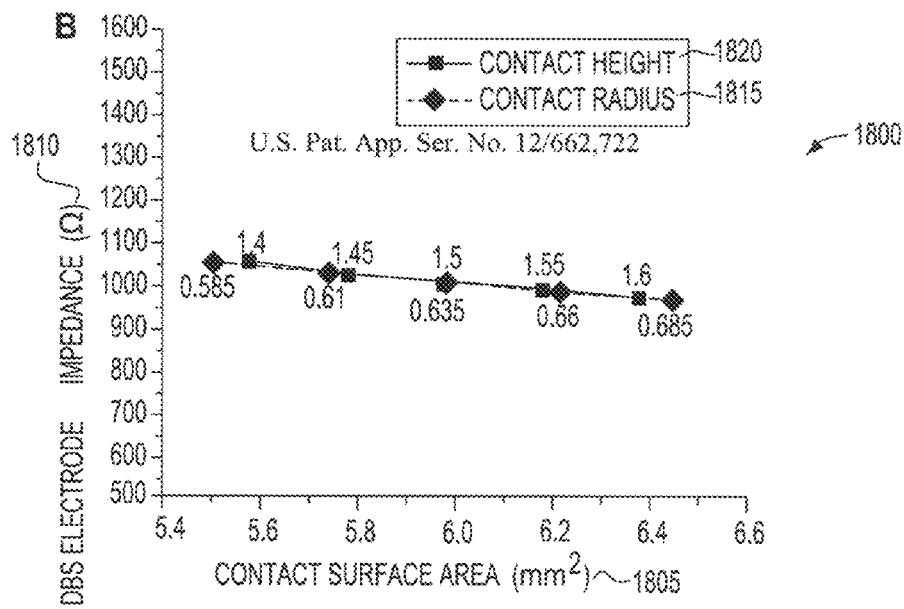
FIG. 18 illustrates generally an example of a relationship illustrating variance in impedance ($\Omega$) resulting from changes in the contact surface area ($mm^2$).

FIG. 18 illustrates generally an example of a relationship 1800 illustrating variance in the DBS electrode impedance ($\Omega$) 1810 resulting from changes in the contact surface area ($mm^2$) 1805 (e.g., variance from manufacturing tolerances). The DBS electrode impedance ($\Omega$) 1810 varied by $\Delta Z \approx 85\Omega$, with the DBS electrode impedance values equally sensitive to changes in either contact radius 1815 (e.g., electrode contact radius (r) 1607) or contact height 1820 (e.g., electrode contact height (h) 1606. Results are shown for DBS electrode impedance as a function of surface area as height and radius are varied +/−0.1 mm from their standard values. By combining the smallest and largest combinations of height and radius, DBS electrode impedance values were calculated of 1094$\Omega$ for d=1.17 mm, h=1.4 mm and 922$\Omega$ for d=1.37 mm, h=1.6 mm ($\Delta Z \approx 172\Omega$). Hence, manufacturing variability in electrode dimensions may contribute to clinically-observed DBS electrode impedance variability.

iii. Effects of Conductivity on Impedance

Figure 19:
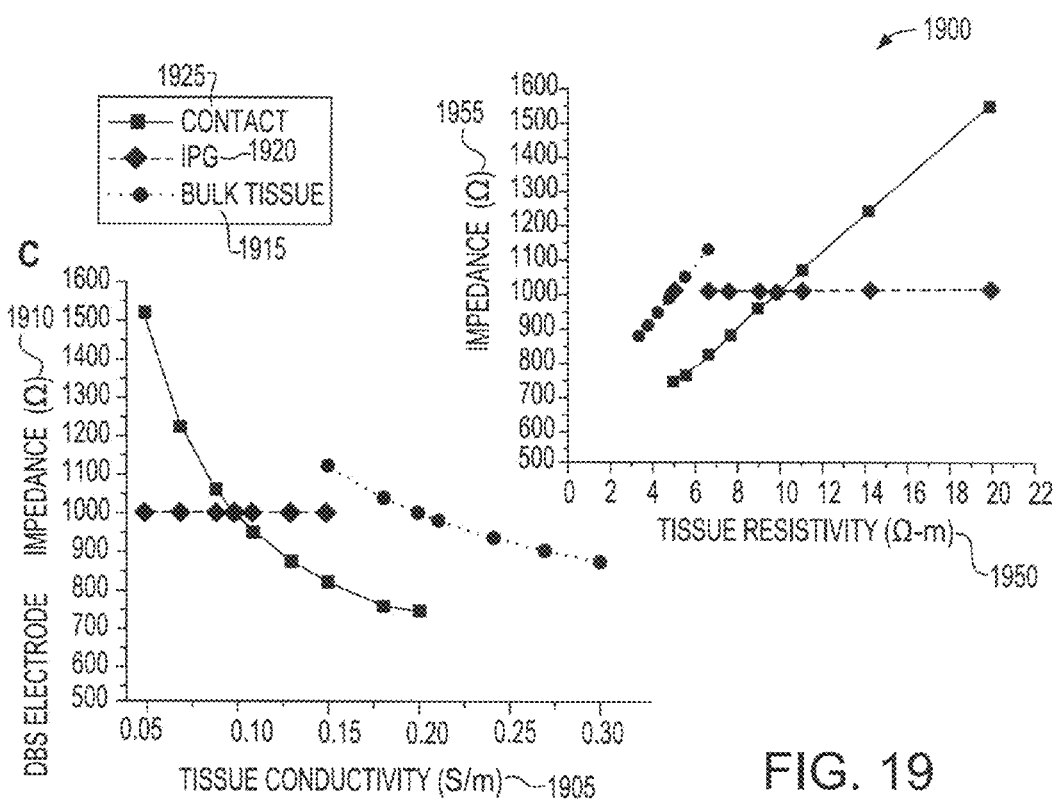
FIG. 19 illustrates generally an example of a relationship illustrating variance in impedance ($\Omega$) resulting from changes in tissue conductivity (S/m) over the range 0.15-0.3 S/m for the bulk tissue, over the range 0.05-0.15 S/m for the encapsulation around the IPG, and over the range 0.05-0.2 S/m around the electrode contact.

FIG. 19 illustrates generally an example of a relationship 1900 illustrating variance in the DBS electrode impedance ($\Omega$) 1910 resulting from changes in tissue conductivity (S/m) 1905 over the range 0.15-0.3 S/m for the bulk tissue 1915 (e.g., tissue conductivity ($\sigma_T$) 1622), over the range 0.05-0.15 S/m for the encapsulation around the IPG 1920 (e.g., IPG encapsulation conductivity ($\sigma_{Ea}$) 1626), and over the range 0.05-0.2 S/m around the electrode contact 1925 (e.g., contact encapsulation conductivity ($\sigma_{Ec}$) 1624). Over the examined ranges, increasing conductivity in the bulk tissue medium decreased the DBS electrode impedance ($\Omega$) 1910 by $\Delta Z \approx 250\Omega$ and increasing conductivity of the electrode lead encapsulation decreased the DBS electrode impedance ($\Omega$) 1910 by $\Delta Z \approx 800\Omega$. In contrast, encapsulation around the IPG had almost no effect with a change in the DBS electrode impedance ($\Omega$) 1910 of $\Delta Z < 1\Omega$.

At the inset of FIG. 19, the relationship between tissue resistivity ($\Omega$-m) 1950 and the DBS electrode impedance ($\Omega$) 1955 is illustrated. Hence, the bulk tissue 1915 (e.g., tissue conductivity ($\sigma_T$) 1622) and the electrode contact 1925 (e.g., contact encapsulation conductivity ($\sigma_{Ec}$) 1624) will likely have a strong effect on clinically-observed DBS electrode impedance.

iv. Effects of Encapsulation Thickness on Impedance

Figure 20:
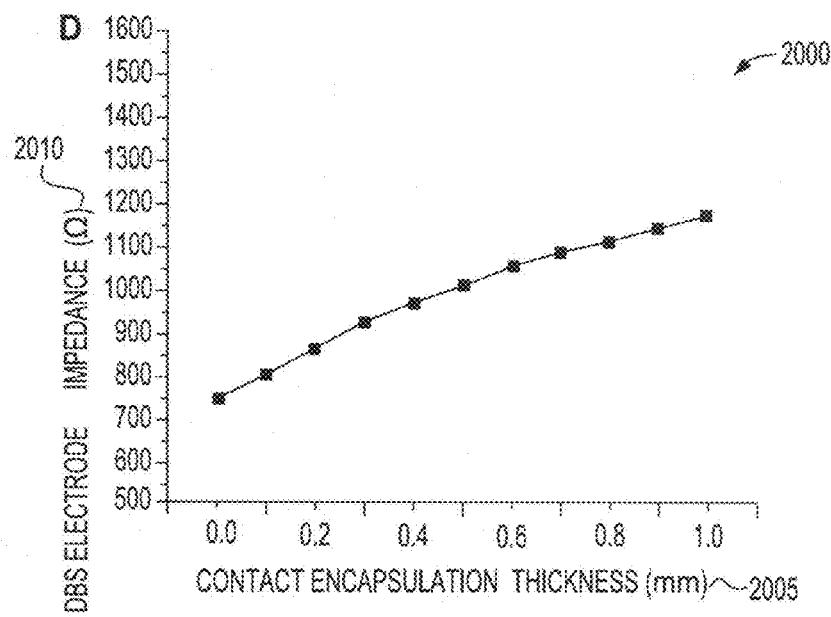
FIG. 20 illustrates generally an example of a relationship illustrating variance in impedance ($\Omega$) resulting from changes in contact encapsulation thickness (mm).

FIG. 20 illustrates generally an example of a relationship 2000 illustrating variance in the DBS electrode impedance ($\Omega$) 2010 resulting from changes in contact encapsulation thickness (mm) 2005. In an example, the encapsulation thickness around the IPG (e.g., IPG Encapsulation thickness ($t_{Ea}$) 1625) had almost no effect on the DBS electrode impedance ($\Omega$) 2010 with a change of $\Delta Z < 1\Omega$ over a range 0 to 1 mm. In contrast, the DBS contact electrode encapsulation thickness 2005 (e.g., electrode encapsulation thickness ($t_{Ec}$) 1623) had a strong effect on the DBS electrode impedance ($\Omega$) 2010. Variations in the contact encapsulation thickness 2005 caused a change in the DBS electrode impedance ($\Omega$) 2010 of $\Delta Z \approx 450\Omega$. Hence, the encapsulation around the electrode lead (e.g., the contact encapsulation thickness 2005 or the electrode encapsulation thickness ($t_{Ec}$) 1623), but not the encapsulation thickness around the IPG (e.g., IPG Encapsulation thickness ($t_{Ea}$) 1625) had a strong effect on DBS electrode impedance.

v. Clinically Relevant Impedance Models

Figure 21:
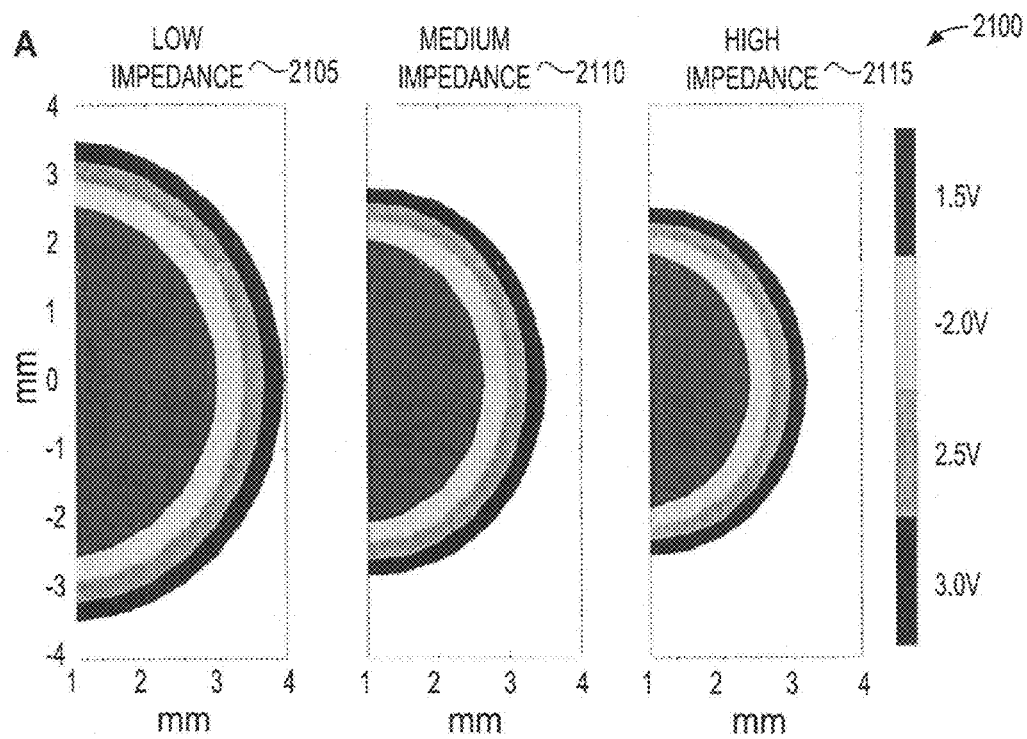
FIG. 21 illustrates generally examples of stimulation results including results from various models compiled according to the magnitude of their effects.

FIG. 21 illustrates generally examples of stimulation results 2100 including results from various models compiled according to the magnitude of their effects. In this example, three models were constructed to represent the range of impedance values observed clinically: (1) a low impedance model 2105; (2) a medium impedance model 2110; and (3) a high impedance model 2115. These three models were then used in simulations to evaluate the effect of impedance changes on the VTA. In this example, each model was stimulated with various DBS stimulus settings (e.g.: −1.5 V, −2 V, −2.5 V, or −3 V pulse amplitude; 130 Hz; and a 90 µs pulse width). In this example, the low impedance model 2105 has the following parameters: 741$\Omega$, $\sigma_{Ec}$=0.2 S/m, $t_{Ec}$=0.5 mm; the medium impedance model 2110 has the following parameters: 1003$\Omega$, $\sigma_{Ec}$=0.1 S/m, $t_{Ec}$=0.5 mm; and the high impedance model 2115 has the following parameters: 1244$\Omega$, $\sigma_{Ec}$=0.07 S/m, $t_{Ec}$=0.5 mm.

vi. Impedance Modulates Shape and Extent of the VTA

In the example of FIG. 21, the low, medium, and high impedance models 2105, 2110, 2115 generated substantially different VTAs with clinically relevant stimulation parameter settings (e.g.: −1.5 V to −3 V pulse amplitude; 90 µs pulse duration; and 130 Hz stimulus train). The spread of activation for the VTA was inversely correlated with the impedance value. In this example, the VTA volumes included 230 $mm^3$, 146 $mm^3$, and 110 $mm^3$ for the low, medium and high impedance models at −3V stimulation, respectively. The reduction in VTA volume with increasing impedance was related to the reduction in both the vertical and lateral spread of the stimulus. Current densities at the electrode contact, and the corresponding charge densities, were also inversely correlated with impedance values. The average charge densities for −3V, 90 µs stimulus pulses in the low, medium and high impedance models were 6, 4.5 and 3.6 µC/$cm^2$/phase, respectively. These values are well below a 30 µC/cm2/phase limit for safe stimulation, but will typically increase linearly with increases in voltage or pulse width.

Figure 22:
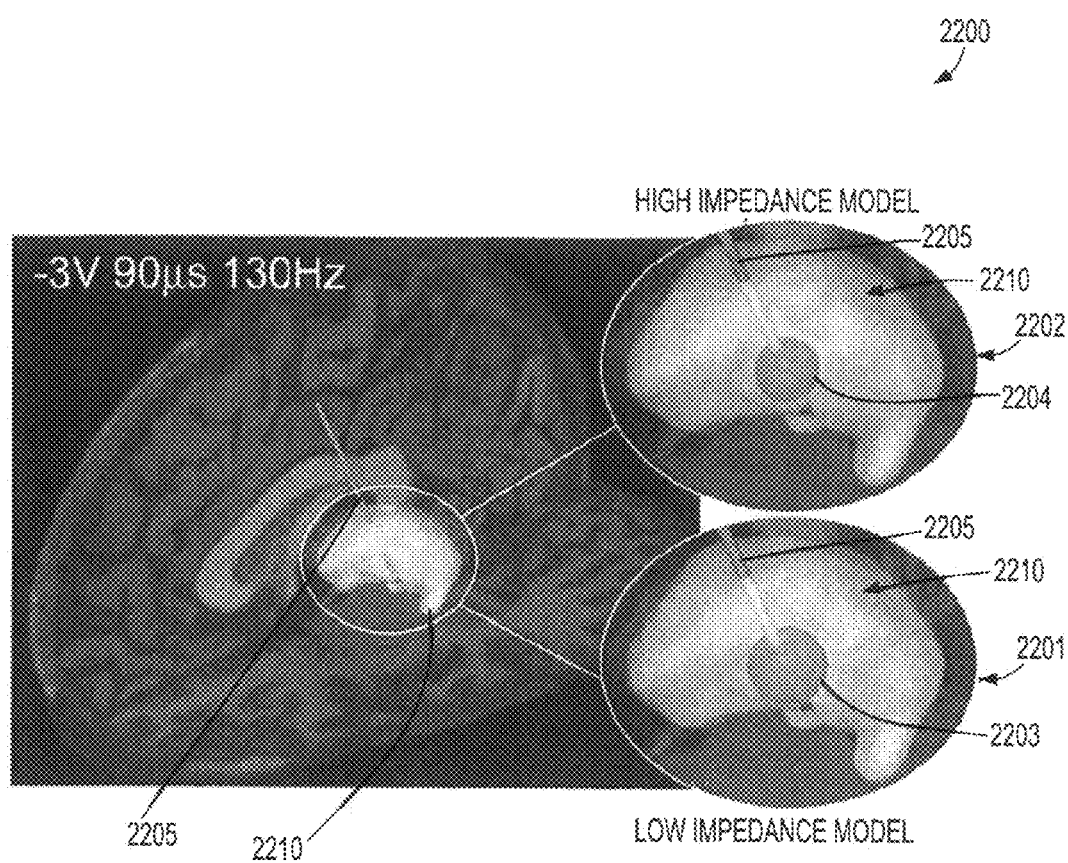
FIG. 22 illustrates generally an example of an illustration including three dimensional renderings of the VTAs for a low impedance model and a high impedance model.

FIG. 22 illustrates generally an example of an illustration 2200 including three dimensional renderings of the VTAs for a low impedance model 2201 and a high impedance model 2202. In this example, for comparison purposes, the exemplary three-dimensional renderings of the VTAs for the low impedance model 2201 (e.g., the low impedance model 2105 of FIG. 21) and the high impedance model 2202 (the high impedance model 2115 of FIG. 21) (VTA 2203 and VTA 2204 for the low impedance model 2201 and the high impedance model 2202, respectively) are shown, in the context of thalamic DBS, in response to a −3 V stimulation pulse. In this example, an electrode 2205 (e.g., the Medtronic 3387-89 DBS electrode) is shown implanted in the thalamus 2210, relative to the sagittal and axial MRI slices D. Discussion of Exemplary Results Generally, the electrode impedance influences the current delivered to the tissue during voltage-controlled DBS. Much of the impedance variability recorded with clinical DBS devices can be accounted for with varying degrees of tissue encapsulation. Impedance values are typically most sensitive to the thickness and conductivity of the encapsulation around the electrode contact. Lower encapsulation conductivities and thicker encapsulation layers can reduce the VTA by increasing the voltage gradient within the encapsulation, thereby decreasing the stimulating influence of the applied electric field within the bulk tissue medium. Clinically relevant impedance variability can substantially alter the VTA size and shape for typical therapeutic stimulation parameter settings. Therefore, attempts to quantify the spread of stimulation in DBS should explicitly incorporate electrode impedance in the calculations and consideration should be given to the electrode impedance when selecting therapeutic stimulation parameter settings for individual subjects.

Sources of impedance variability can include the variance in the volume of a conductor and the size of an electrode. Other sources could also have substantial effects on impedance, including wire impedance (e.g., the ~80Ω impedance of the Medtronic lead and extension wiring), which can increase dramatically due to poor mechanical or electrical coupling between the IPG and the extension, or between the extension and lead. Additionally, in certain examples, each of the four individual wires within the extension and lead can be made up of a group of individual filars, and breakage of one or more of these filars can dramatically increase resistance. Increases in impedance resulting from these hardware issues can reduce the voltage drop within the tissue medium, which can reduce the VTA.

In other examples, monopolar stimulation and bipolar stimulation can result in different impedance values. For example, an axisymmetric model of DBS predicts that impedance values during bipolar stimulation will be higher than during monopolar stimulation. In certain bipolar stimulation examples, in a model of cathode and anode on adjacent electrode contacts, the Medtronic 3389 electrode (0.5 mm contact spacing) and the Medtronic 3387 electrode (1.5 mm contact spacing) had model impedances of 1478Ω and 1641Ω, respectively. Adding an inactive contact between the cathode and anode increased the impedance to >2000Ω for both electrode types. Like the monopolar stimulation results, bipolar impedances were most strongly influenced by the encapsulation layer around the electrode contact, and by the tissue conductivity.

An axisymmetric model of DBS can simulate a chronic and stable DBS electrode-tissue interface. The use of homogeneous isotropic subdomains of the encapsulation and bulk tissue medium are simplifications of the three-dimensionally complex tissue micro- and macro-structure surrounding implanted electrodes. A more accurate representation of the tissue medium will undoubtedly introduce additional variability in the impedance. Further, the electrode surface of the model is typically smooth; it neglects any electrode corrosion and resulting surface modification that may occur due to prolonged stimulation. Hence, the surface area specified in the electrode models may underestimate the actual surface area of clinical electrodes, however, analysis of post-mortem or explanted DBS electrodes generally does not show any visible surface modification of the metal electrode contacts.

Tissue conductivity generally influences DBS impedance measurements; however, a great deal of variability exists in estimates of tissue conductivity. Mean values typically include 0.15 S/m for white matter, 0.45 S/m for gray matter and 0.17 S/m as a mean conductivity. In other examples, however, mean conductivity is estimated as 0.3 S/m. Moreover, variation in human brain conductivity or tissue impedances can generally vary up to 33.3% from subject-to-subject.

An additional source of variability can include the conductivity of the electrode encapsulation. Encapsulation is generally the final stage of the body's reaction to the presence of a foreign body, in which the body attempts to destroy or isolate any non-native substance. The tissue response typically includes both an early anti-inflammatory response due to insertion trauma, and a sustained response induced in part by one or more of micromotion, tethering, and device biocompatibility. Generally, encapsulation thickness around the DBS electrode lead is believed to be at least 25 µm and typically not greater than 1 mm. Tissue changes around the active contact and non-stimulated areas adjacent to the insulated parts of the lead generally do not differ. In certain examples, a thin inner capsule of connective tissue can develop around the lead track. The thickness of this fibrous sheath typically ranges from 5 to 25 µm, with little to no correlation to duration of stimulation. A narrow rim of fibrillary gliosis of less than 500 µm can abut the fibrous capsule. In other examples, in the nearby brain tissue, loosely scattered glial fibrillary acidic protein-positive protein astrocytes can develop in a small area. As such, the clinical long-lasting benefit of DBS can correlate to the absence of progressive gliotic scar formation. Nevertheless, gliosis or the giant cell reaction can alter tissue impedance and thereby distort current distribution.

Further, stimulation can transiently decrease electrode impedance. In an example, a ~430Ω difference can develop between active and inactive DBS contacts during chronic stimulation. Further, a reversible drop in impedance can occur when contacts are activated with monopolar stimulation over a period of several days. However, when the contact is deactivated, the impedance can return to the pre-stimulation values. Generally, the most substantial and consistent impedance change comes from protein adsorption and the cellular layers surrounding the electrode. In turn, stimulation through a given contact can modify the tissue microstructure of the local encapsulation, increasing conductivity and decreasing electrode impedance.

Generally, impedance values can be calculated using Ohm's law. Specifically, the voltage at the onset of the cathodic stimulation pulse can be divided by the current, where current can be calculated by integrating the current density across the electrode contact. In certain examples, in which the IPG case and a DBS electrode were connected with a 1 kΩ resistor, a Medtronic programmer accurately reported the resistance value with the stimulation parameters −1.5 V, 210 µsec, 30 Hz. However, the measured impedance was a function of both the voltage and pulse width generated by the Medtronic IPG. Increases in either parameter generally caused a decrease in the measured impedance—most likely due to the way the Medtronic programmer measures impedance from the time-dependent voltage waveform.

Generally, the clinical impedance measurements from DBS electrodes can depend on many factors, some of which cannot be directly measured. However, our analysis suggests that much of the 500-1500Ω range seen clinically can be accounted for by using a realistic variability in the electrical properties of the electrode encapsulation and bulk tissue medium. Impedance changes within this clinically-observed range can directly affect the size and shape of the VTA. In turn, attempts to quantify the stimulation effects of DBS on a subject-by-subject basis should explicitly account for the measured electrode impedance.

Figure 23:
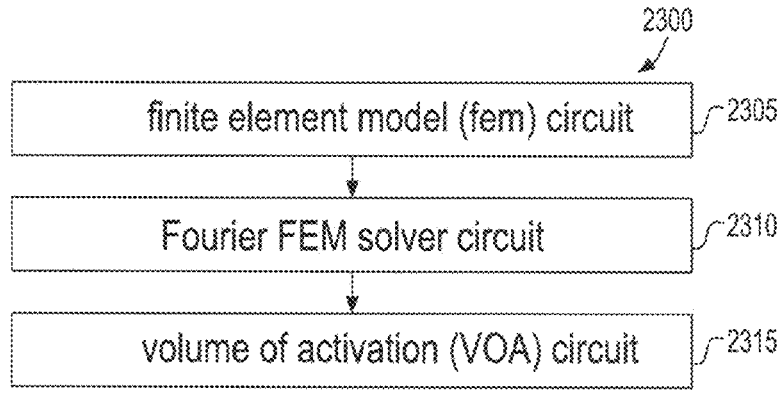
FIG. 23 illustrates generally an example of a system including a finite element model (FEM) circuit, a Fourier FEM solver circuit, and a volume of activation (VOA) circuit.

FIG. 23 illustrates generally an example of a system 2300 including a finite element model (FEM) circuit 2305, a Fourier FEM solver circuit 2310, and a volume of activation (VOA) circuit 2315. In certain examples, at least a portion of the system 2300 can be implemented using a processor circuit, such as a microprocessor configured to perform instructions to implement one or more circuits described herein.

In an example, the FEM circuit 2305 can be configured to create a FEM of an implanted electrode and a tissue medium in which the electrode is implanted. Generally, the FEM can include an electrical model of the electrode and the tissue medium. The electrode can be configured to deliver an energy to a subject, such as to at least a portion of a brain (e.g., a thalamus, a subthalamic nucleus (STN), or other portion of the brain). In an example, the electrode can include at least one electrode 105, a neurostimulation electrode, or one or more other electrodes. The tissue medium can include at least a portion of the brain, such as the thalamus, the STN, or other portion of the brain. In certain examples, the FEM can include certain relationships, such as electrical relationships (e.g., capacitive, inductive, conductive, or other electrical relationships), between the components in the FEM, such as the electrode or the tissue medium. In an example, the FEM can include an electrode-tissue interface. The electrode-tissue interface can include an encapsulation layer around the electrode. In an example, the FEM circuit 2305 can include an axisymmetric FEM circuit (e.g., see FIG. 16). In this way, the FEM can be used to provide an electrical model of the implanted electrode and the tissue medium.

In the example of FIG. 23, the Fourier FEM solver circuit 2310 can be configured to calculate a potential distribution in the tissue medium using information from the FEM circuit, such as the FEM, and a capacitive component of at least one of the electrode and the tissue medium. In an example, the information from the FEM circuit includes the capacitive component of the at least one of the electrode and the tissue medium. In another example, the Fourier FEM solver circuit 2310 can be configured to calculate a potential distribution in the tissue medium using information from the FEM circuit and a capacitive component of at least one of the electrode, the tissue medium, and the electrode-tissue interface.

In certain examples, the Fourier FEM solver circuit 2310 can be configured to calculate the potential distribution in the tissue medium in both time and space. Generally, the Fourier FEM solver circuit 2310 can be configured to calculate the potential distribution in the tissue medium using the Poisson equation and the FEM.

In an example, the Fourier FEM solver circuit 2310 can be configured to separate a stimulus waveform into frequency components, to obtain a solution of the Poisson equation at at least one frequency component by using a stiffness matrix with a complex component such as $(\sigma+i\omega)$, and to use the solution to reassemble the stimulus waveform. Generally, the stimulus waveform can include any energy delivered to the tissue medium using the implanted electrode, such as a neurostimulation energy. In certain examples, the system is configured to receive user input defining an arbitrary stimulus waveform of interest. Further, the stiffness matrix $(\sigma+i\omega)$ is typically configured to include a representation of at least one capacitive component of at least one of the implanted electrode and the tissue medium. In an example, the stiffness matrix $(\sigma+i\omega)$ can include a representation of the capacitive component of the electrode-tissue interface. In various examples, capacitive components of the implanted electrode or the tissue medium can be calculated individually for a particular subject, can be deduced from one or more clinical studies, or can be estimated using clinical data or other information.

In this example, the VOA circuit 2315 can be configured to predict a VOA, such as by using the potential distribution and a neuron model. In certain examples, the neuron model can include a multi-compartment neuron model, or a multi-compartment neuron cable model of myelinated axons. In an example, the VOA circuit 2315 can be configured to interpolate the potential distribution onto a plurality of model axons. The VOA circuit 2315 can be configured to predict a VOA, such as a VOA for a particular FEM, using one or more stimulation waveforms (e.g., a −3 V stimulation pulse, a −2 V stimulation pulse, and a −1 V stimulation pulse, or other configurations) or one or more combinations of different stimulation parameters.

Figure 24:
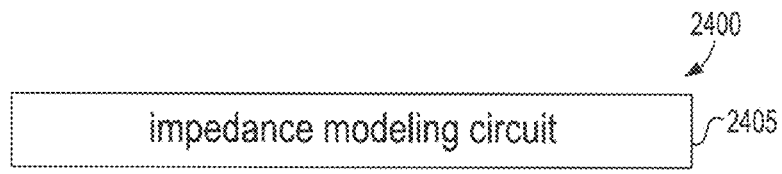
FIG. 24 illustrates generally an example of a system including an impedance circuit.

FIG. 24 illustrates generally an example of a system 2400 including an impedance modeling circuit 2405. The impedance modeling circuit 2405 can be configured to estimate an impedance, such as an effective impedance of an implanted electrode (e.g., a DBS electrode). In certain examples, the impedance modeling circuit 204 estimates the impedance of the implanted electrode by dividing a stimulation voltage by an integrated current density along a modeled active implanted electrode contact. In certain examples, the potential distribution can be calculated using the estimated effective electrode impedance. In other examples, other impedances can be used to calculate the potential distribution, including a wire impedance, or other impedances (e.g., see FIG. 16).

Figure 25:
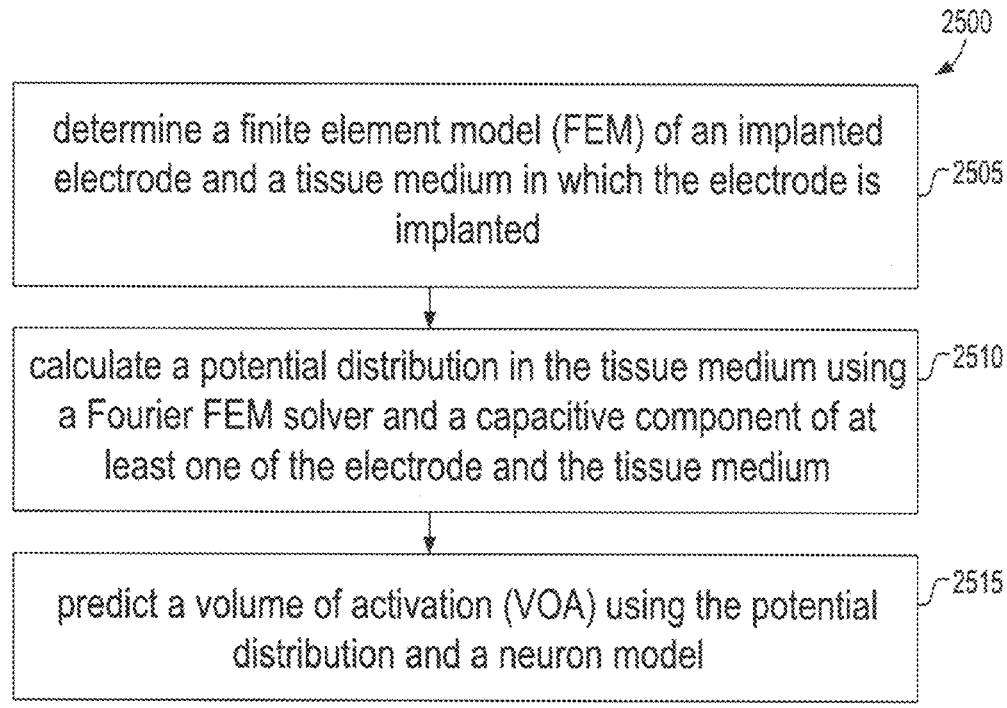
FIG. 25 illustrates generally an example of a method including determining a finite element model (FEM), calculating a potential distribution in the tissue medium, and predicting a volume of activation (VOA).

FIG. 25 illustrates generally an example of a method 2500 including determining a finite element model (FEM) of an implanted electrode and a tissue medium in which the electrode is implanted, calculating a potential distribution in the tissue medium, and predicting a volume of activation (VOA). In the method 2500, the potential distribution can be calculated using a Fourier FEM solver and a capacitive component of at least one of the electrode and the tissue medium. Predicting a VOA can include using the potential distribution and a neuron model.

At 2505, a FEM of an implanted electrode and a tissue medium in which the electrode is implanted is determined. Generally, the FEM can include an electrical model of the electrode and the tissue medium. In an example, the FEM can include an electrical model of an electrode-tissue interface, which can include an encapsulation layer around the electrode. In certain examples, the FEM can include certain relationships, such as electrical relationships (e.g., capacitive, inductive, or other electrical relationships), between the components in the FEM, such as the electrode or the tissue medium. In an example, the FEM can be determined using multiphysics modeling software, such as FEMLAB 3.1.

At 2510, a potential distribution in the modeled tissue medium is calculated using a Fourier FEM solver and a capacitive component of at least one of the electrode and the tissue medium. In an example, the potential distribution can be calculated using the Fourier FEM solver and a capacitive component of at least one of the electrode, the tissue medium, and the electrode-tissue interface. The Fourier FEM solver can be used to combine the desired DBS stimulation waveform and the capacitance of the electrode-tissue interface into the bioelectric field model. In an example, the potential distribution in the modeled tissue medium can be calculated by solving a Poisson equation, such as by using direct matrix inversion.

At 2515, a VOA is predicted using the potential distribution and a neuron model. In an example, by applying the potential distribution to the neuron model (e.g., by establishing an activation threshold for each axon and applying the potential distribution to the threshold relationship) the VOA can be predicted (e.g., see FIG. 4).

Figure 26:
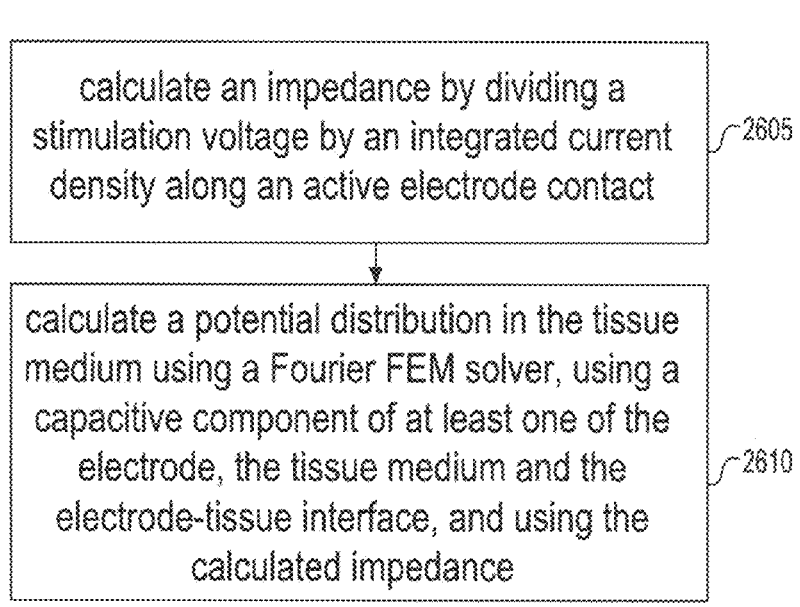
FIG. 26 illustrates generally an example of a method including calculating an impedance and calculating a potential distribution in the tissue medium.

FIG. 26 illustrates generally an example of a method 2600 including calculating an effective electrode impedance (e.g., an implanted DBS electrode impedance) and calculating a potential distribution in the modeled tissue medium. In this example, the calculating the potential distribution in the modeled tissue medium includes using a Fourier FEM solver, using a capacitive component of at least one of the modeled implanted electrode and the modeled tissue medium, modeling an encapsulation layer around the implanted electrode, and using the calculated effective electrode impedance. Calculating the electrode impedance can include dividing a modeled stimulation voltage by a modeled integrated current density along a surface of a modeled active implanted electrode contact, where the active implanted electrode contact includes a contact from which a stimulation is being delivered.

At 2605, an effective electrode impedance is calculated, such as by dividing a modeled stimulation voltage by a modeled integrated current density along a modeled active implanted electrode contact. In an example, a model can be created (e.g., see FIG. 16) using the calculated impedance. In certain examples, the calculated impedance can include one or more of an effective electrode impedance, a wire resistance (e.g., $R_{ext}$ 1651 and $R_{Lead}$ 1652), an electrode encapsulation layer impedance (e.g., $R_{ec}$ 1659), or other impedances.

At 2610, a potential distribution is calculated in the modeled tissue medium using a Fourier FEM solver, including using a modeled capacitive component of at least one of the electrode, the tissue medium, and the electrode-tissue interface (e.g., an encapsulation layer around the implanted electrode), and using the calculated impedance. Generally, modeling such impedances can increase the correlation between a clinically measured VOA and a model-derived VOA, making the model more useful for predicting clinical results.

Figure 27:
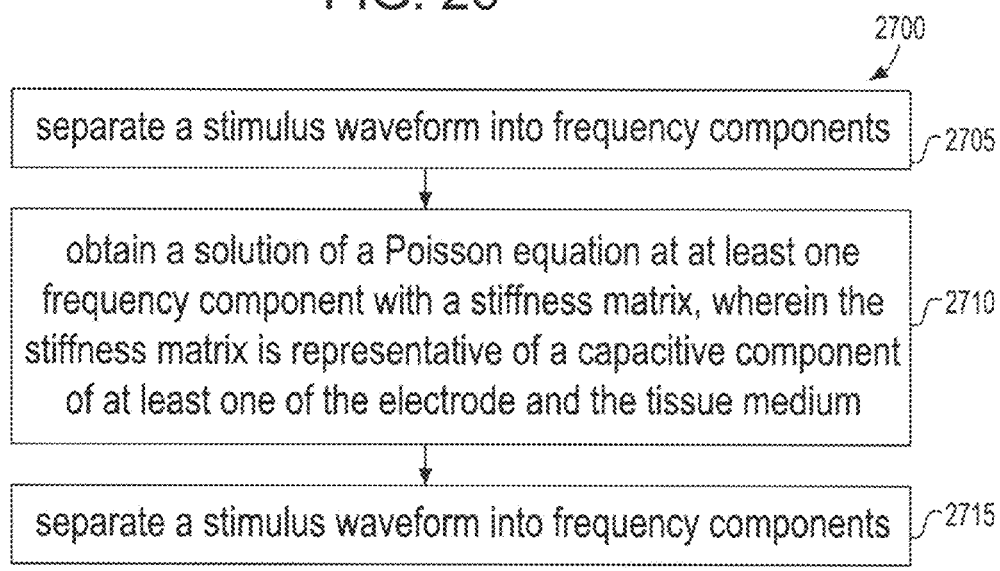
FIG. 27 illustrates generally an example of a method including separating a stimulus waveform into frequency components, obtaining a solution of a Poisson equation at least one frequency component with a stiffness matrix, and using the solution to reassemble the stimulus waveform.

FIG. 27 illustrates generally an example of a method 2700 including separating a stimulus waveform into frequency components, obtaining a solution of a Poisson equation of at least one frequency component by using a stiffness matrix ($\sigma+i\omega$), and using the solution to reassemble the stimulus waveform. The stiffness matrix ($\sigma+i\omega$) can include a representation of a capacitive component of at least one of the electrode and the tissue medium. In an example, the stiffness matrix ($\sigma+i\omega$) can include a representation of a capacitive component of an electrode-tissue interface.

At 2705, an arbitrary desired stimulus waveform is separated into frequency components. In an example, the desired stimulation waveform (or a DBS waveform) can be created or specified in the time domain. The stimulation waveform can be separated into frequency components, or converted into the frequency domain, such as by using a Fourier transform or other similar operator (e.g., FFT).

At 2710, a solution of a Poisson equation is obtained for at least one frequency component, such as by using a stiffness matrix ($\sigma+i\omega$), wherein the stiffness matrix ($\sigma+i\omega$) includes a representation of a capacitive component of at least one of the implanted electrode and the tissue medium. In an example, the stiffness matrix ($\sigma+i\omega$) can include a representation of a capacitive component of the electrode-tissue interface. Generally, the Poisson equation can be understood as a partial differential equation that can be used to calculate an electric potential for a given charge distribution. In this example, a desired stimulation waveform is given. In an example, the Poisson equation can generally be used to distribute the effects of the FEM model onto the stimulus waveform.

At 2715, the solution is used to reassemble the stimulus waveform. In an example, the stimulus waveform is reassembled in the time domain to apply the stimulus waveform to the tissue medium. By applying the reassembled stimulation waveform to the tissue medium, the potential distribution in the tissue medium can be calculated.

Figure 28:
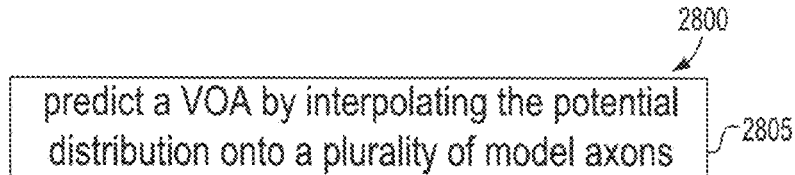
FIG. 28 illustrates generally an example of a method including predicting a volume of activation (OVA) by interpolating the potential distribution onto a plurality of model axons.

FIG. 28 illustrates generally an example of a method 2800 including predicting a volume of activation (VOA) by interpolating the potential distribution onto a plurality of model axons.

At 2805, a VOA is predicted by interpolating the potential distribution onto a plurality of model axons. In an example, the potential distribution can be interpolated onto a plurality of model axons (e.g., a length of a cable model, etc.). Using neural simulation software (e.g., NEURON v5.7), VOA (or volume of tissue activated (VTA)) can be calculated using the interpolated potential distribution.

Figure 29:
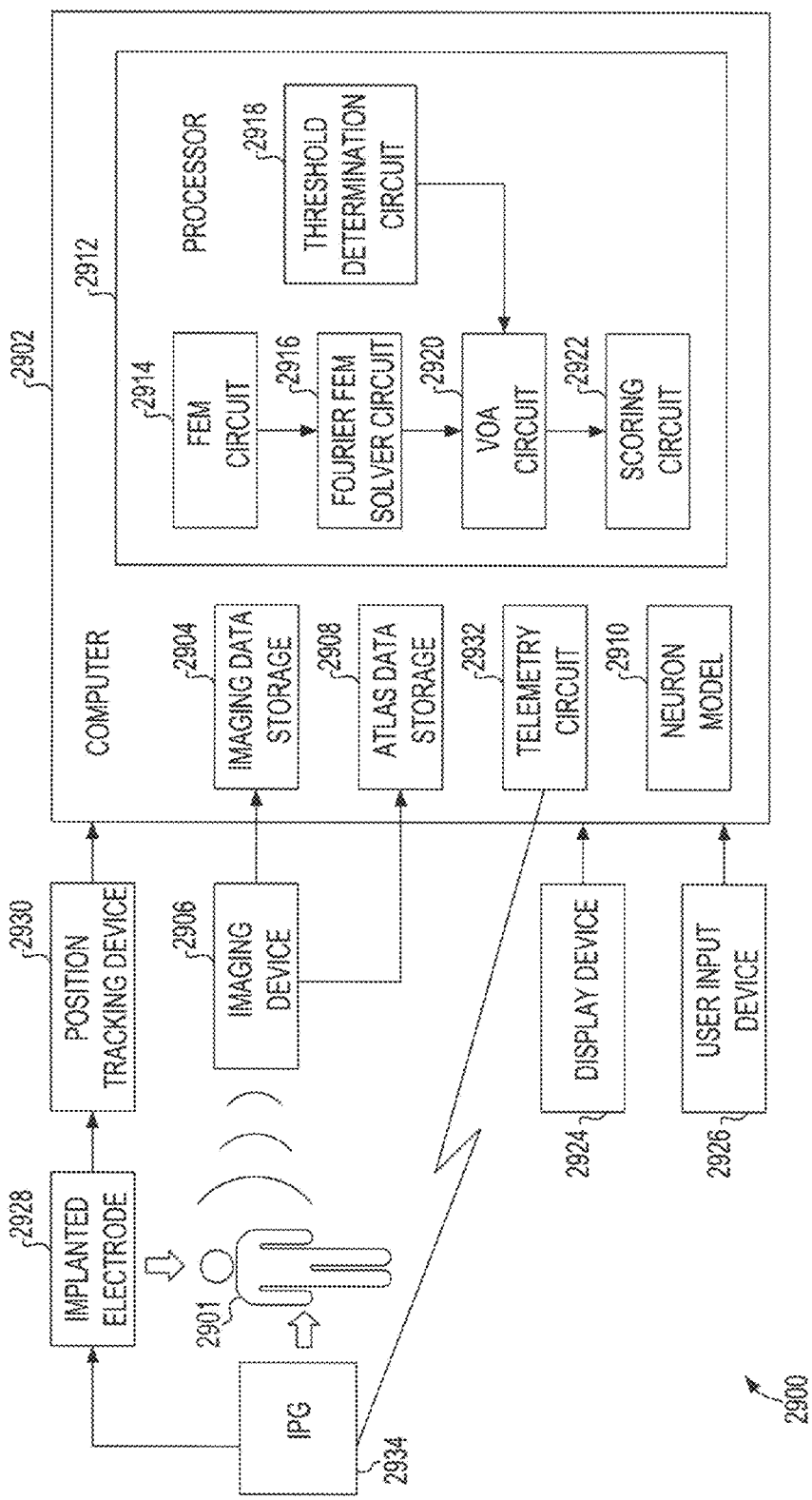
FIG. 29 illustrates generally an example of a system for performing at least some of the methods discussed above for deep brain stimulation (DBS) or other stimulation of a subject.

FIG. 29 illustrates generally an example of a system 2900 for performing at least some of the methods discussed above for DBS or other stimulation of a subject 2901. As described above, the stimulation can be of the central nervous system (brain or spinal cord) or the peripheral nervous system, including cranial nerves, spinal nerves, sympathetic nerves and ganglia, and/or parasympathetic nerves and ganglia. In an example, the system 2900 can include an image-guided surgical (IGS) workstation or other computer 2902, such as that described in the commonly assigned McIntyre et al. U.S. patent application Ser. No. 10/885,982 entitled "BRAIN STIMULATION MODELS, SYSTEMS, DEVICES, AND METHODS," (herein "McIntyre et al. '982") which is hereby incorporated by reference in its entirety, including its disclosure of performing methods for DBS or other stimulation of a subject.

In this example, the computer 2902 can include an imaging data storage 2904, configured to receive imaging data from a medical imaging device 2906, a DTI or other atlas data storage 2908, a neuron or axon model 2910 (e.g., such as discussed above or in McIntyre et al. '982), a processor 2912, and a telemetry circuit 2932. In an example, the processor 2912 can include a finite element model (FEM) circuit 2914, a Fourier FEM solver circuit 2916, a threshold determination circuit 2918, a volume of activation (VOA) 2920 circuit, and a scoring circuit 2922. In this example, the FEM circuit 2914 can be configured to create a FEM of an implanted electrode and a tissue medium, via a processor. The Fourier FEM solver circuit 2916 can be configured to calculate, via a processor a potential distribution in the tissue medium using information from the FEM circuit and a capacitive component of at least one of the implanted electrode and the tissue medium. In certain examples, the Fourier FEM solver circuit 2916 can be configured to calculate the potential distribution in the tissue medium using an encapsulation area around the implanted electrode, or using a calculated impedance, as described above. The threshold determination circuit 2918 can be used to develop a threshold value of the calculated potential distribution. The VOA circuit 2920 can be configured to predict, via a processor, a VOA using the potential distribution (e.g., such as discussed above or in McIntyre et al. '982). The scoring circuit 2922 can be configured to compare the predicted VOA against one or more desired or undesired anatomic regions to determine whether the VOA will perform as desired, as discussed in McIntyre et al. '982.

In an example, the VOA can be displayed using a display device 2924, such as together with other data that is typically displayed on an IGS workstation display, as discussed in McIntyre et al. '982. A user input device 2926 can be configured to permit a user to input data, for example, particular information about the configuration or morphology of the implanted electrode 2928 (or other electrode) being used in the procedure. In one example, a position tracking device 2930 can track the location of the implanted electrode 2928 so that the location can be displayed on the display device 2924, such as with the VOA or scoring information discussed above or in McIntyre et al. '982. In an example, the telemetry circuit 2932 can be configured to program or otherwise communicate with an IPG, such as to adjust electrical stimulation parameters using the VOA or scoring information discussed above or in McIntyre et al. '982. Although FIG. 29 illustrates an IGS workstation example, it is understood that portions of the system 2900 could alternatively be implemented outside the context of an IGS workstation such as, for example, in an external programmer device for an implantable DBS controller circuit 2934. Such an alternate example need not include any intraoperative imaging or position tracking.

Various examples above can be performed using a machine-readable medium or a computer-readable medium, which includes any medium which is capable of storing or encoding a sequence of instructions for being performed by the machine to perform one or more of the methods described herein.

Various examples described herein may be computer-implemented. Some examples may include hardware computer-readable media encoded with a computer program (e.g., software), which includes instructions operable to cause an electronic device to perform methods of various examples. For example, the present invention provides for a program storage device readable by a machine, tangibly embodying a program of instructions executable by the machine to perform method steps as described herein. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. The computer-readable media is non-transitory in that it comprises all computer-readable media, with the sole exception being a transitory, propagating signal.

It is to be understood that the above description is intended to be illustrative, and not restrictive. For example, the above-described examples (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A computer system comprising:
a processor that is configured to execute:
 a finite element model (FEM) module to determine a FEM that models an implanted electrode and a spinal cord in which the electrode is implanted;
 a Fourier FEM solver module to calculate a potential distribution in the spinal cord using information obtained by the execution of the FEM module and a capacitive component of at least one of the electrode and the spinal cord, wherein, with the execution of the Fourier FEM solver module, the processor is configured to:
  separate a stimulus waveform into frequency components;
  obtain a solution of a Poisson equation at at least one frequency component with a stiffness matrix $(\sigma+i\omega)$, wherein the stiffness matrix is representative of the capacitive component of the at least one of the electrode and the spinal cord; and
  use the solution to reassemble the stimulus waveform; and
 a volume of activation (VOA) module to provide a predicted VOA using the potential distribution and a neuron model.

2. The system of claim 1, wherein, with the execution of the Fourier FEM solver module, the processor is configured to calculate the potential distribution in the spinal cord using information obtained by the execution of the FEM module and the capacitive component of the electrode.

3. The system of claim 1, wherein, with the execution of the Fourier FEM solver module, the processor is configured to calculate the potential distribution in the spinal cord using information obtained by the execution of the FEM module and the capacitive component of the spinal cord.

4. The system of claim 1, wherein:
with the execution of the FEM module, the processor is configured to determine a FEM that models the electrode, the spinal cord, and an electrode-tissue interface; and
with the execution of the Fourier FEM solver module, the processor is configured to calculate the potential distribution in the spinal cord using information obtained by the execution of the FEM module and the capacitive component of at least one of the electrode, the spinal cord, and the electrode-tissue interface.

5. The system of claim 4, wherein, with the execution of the Fourier FEM solver module, the processor is configured to calculate the potential distribution in the spinal cord using information obtained by the execution of the FEM module and the capacitive component of the electrode-spinal cord interface.

6. The system of claim 5, wherein the electrode-spinal cord interface includes an encapsulation area around the electrode.

7. The system of claim 1, wherein, with the execution of the Fourier FEM solver module, the processor is configured to calculate the potential distribution in the spinal cord in both time and space.

8. The system of claim 1, wherein, with the execution of the VOA module, the processor is configured to interpolate the potential distribution onto a plurality of model axons.

9. The system of claim 1, wherein, with the execution of the VOA module, the processor is configured to predict a VOA using multiple stimulation waveforms.

10. The system of claim 1, wherein the processor is configured to:
execute an impedance module to calculate an impedance by dividing a stimulation voltage by an integrated current density along an active electrode contact; and
calculate a potential distribution using the calculated impedance.

11. A non-transitory computer-readable storage medium, including instructions that, when performed by a computer, cause the computer to:
determine a finite element model (FEM) of an implanted electrode and a spinal cord in which the electrode is implanted;
calculate a potential distribution in the spinal cord using a Fourier FEM solver and a capacitive component of at least one of the electrode and the spinal cord, wherein, the calculating includes:
separating a stimulus waveform into frequency components;
obtaining a solution of a Poisson equation at at least one frequency component with a stiffness matrix ($\sigma+i\omega$), wherein the stiffness matrix is representative of the capacitive component of the at least one of the electrode and the spinal cord; and
using the solution to reassemble the stimulus waveform; and
predict a volume of activation (VOA) using the potential distribution and a neuron model.

12. A computer system comprising:
a processor that is configured to:
determine a finite element model (FEM) of an implanted electrode and a spinal cord in which the electrode is implanted;
calculate a potential distribution in the spinal cord using a Fourier FEM solver and a capacitive component of at least one of the electrode and the spinal cord, wherein, the calculating includes:
separating a stimulus waveform into frequency components;
obtaining a solution of a Poisson equation at at least one frequency component with a stiffness matrix ($\sigma+i\omega$), wherein the stiffness matrix is representative of the capacitive component of the at least one of the electrode and the spinal cord; and
using the solution to reassemble the stimulus waveform; and
predict a volume of activation (VOA) using the potential distribution and a neuron model.

13. A computer-assisted method comprising:
determining, by a computer processor, a finite element model (FEM) of an implanted electrode and a spinal cord in which the electrode is implanted;
calculating, by the processor, a potential distribution in the spinal cord using a Fourier FEM solver and a capacitive component of at least one of the electrode and the spinal cord, wherein, the calculating includes:
separating a stimulus waveform into frequency components;
obtaining a solution of a Poisson equation at at least one frequency component with a stiffness matrix ($\sigma+i\omega$), wherein the stiffness matrix is representative of the capacitive component of the at least one of the electrode and the spinal cord; and
using the solution to reassemble the stimulus waveform; and
predicting, by the processor, a volume of activation (VOA) using the potential distribution and a neuron model.

14. The method of claim 13, wherein the calculating the potential distribution in the spinal cord includes using the Fourier FEM solver and the capacitive component of the electrode.

15. The method of claim 13, wherein the calculating the potential distribution in the spinal cord includes using the Fourier FEM solver and the capacitive component of the spinal cord.

16. The method of claim 13, wherein:
the determining the FEM includes determining a FEM of the electrode, the spinal cord, and an electrode-spinal cord interface; and
the calculating the potential distribution in the spinal cord includes using the Fourier FEM solver and a capacitive component of at least one of the electrode, the spinal cord, and the electrode-spinal cord interface.

17. The method of claim 16, wherein the calculating the potential distribution in the spinal cord includes using the Fourier FEM solver and the capacitive component of the electrode-spinal cord interface.

18. The method of claim 17, wherein the using the capacitive component of the electrode-spinal cord interface includes using the capacitive component of an encapsulation layer around the electrode.

19. The method of claim 13, wherein the calculating the potential distribution in the spinal cord includes calculating the potential distribution in the spinal cord in both time and space.

20. The method of claim 13, wherein the using the potential distribution and the neuron model includes interpolating the potential distribution onto a plurality of model axons.

21. The method of claim 13, wherein the predicting the VOA includes using multiple stimulation waveforms.

22. The method of claim 13, including calculating an impedance by dividing a stimulation voltage by an integrated current density along an active electrode contact, wherein the calculating the potential distribution includes using the calculated impedance.

* * * * *